United States Patent
Perfect et al.

(10) Patent No.: US 9,005,988 B2
(45) Date of Patent: Apr. 14, 2015

(54) METHOD TO ASSESS MULTIPHASE FLUID COMPOSITIONS

(75) Inventors: Emma Perfect, Edinburgh (GB); Catherine Rowley-Williams, Linlithgow (GB); Cameron Mackenzie, Glasgow (GB); Artin Moussavi, Hammersmith Grove (GB)

(73) Assignee: Lux Innovate Limited, Edinburgh (GB)

( * ) Notice: Subject to any disclaimer, the term of this patent is extended or adjusted under 35 U.S.C. 154(b) by 536 days.

(21) Appl. No.: 13/003,906

(22) PCT Filed: Jul. 20, 2009

(86) PCT No.: PCT/GB2009/001788
§ 371 (c)(1),
(2), (4) Date: Mar. 10, 2011

(87) PCT Pub. No.: WO2010/007390
PCT Pub. Date: Jan. 21, 2010

(65) Prior Publication Data
US 2011/0151576 A1    Jun. 23, 2011

(30) Foreign Application Priority Data
Jul. 18, 2008    (GB) .................................. 0813277.1

(51) Int. Cl.
| G01N 21/76 | (2006.01) |
| G01N 33/18 | (2006.01) |
| G01N 33/28 | (2006.01) |
| G01N 21/64 | (2006.01) |

(52) U.S. Cl.
CPC ........... *G01N 33/1833* (2013.01); *Y10T 436/25* (2015.01); *G01N 21/6408* (2013.01); *G01N 21/643* (2013.01); *G01N 21/6445* (2013.01); *G01N 21/6458* (2013.01); *G01N 33/2823* (2013.01); *G01N 33/2882* (2013.01); *G01N 2021/6421* (2013.01); *G01N 2021/6432* (2013.01)

(58) Field of Classification Search
None
See application file for complete search history.

(56) References Cited

U.S. PATENT DOCUMENTS

| 5,185,531 A | 2/1993 | Wynn |
| 2004/0098202 A1 | 5/2004 | McNeil et al. |
| 2008/0044543 A1* | 2/2008 | McClements et al. ........ 426/573 |

OTHER PUBLICATIONS

Troup, G.M. A fluorescence Investigation of laterally phase-separated cholesterol rich domains in model lipid membranes using the membrane probe—myristoyl-2-[12-(5-dimethylamino-1-naphthalenesulfonyl)amino]dodecanoyl]-sn-Glycerol-3-phosphocholine, 2004, Doctoral thesis, Drexel University.*

(Continued)

*Primary Examiner* — Robert Xu
(74) *Attorney, Agent, or Firm* — Ostrager Chong Flaherty & Broitman P.C.

(57) ABSTRACT

A method for the assessment of a multiphase (aqueous and organic) sample phase, the method comprising adding at least one detection molecule to the multiphase sample; detecting a signal emitted from the detection molecule/multiphase sample mixture, the signal being detectably different when the at least one detection molecule is present in one of either an organic phase, an aqueous phase or an interface between said organic phase and said aqueous phase of the multiphase sample; and analyzing the detected signal to assess the properties of a phase or an interface between phases. A system for use in such a method, use of at least one detection molecule for the assessment of a multiphase sample, and a composition for use in the assessment of a multiphase sample are also disclosed.

47 Claims, 15 Drawing Sheets

(56) References Cited

OTHER PUBLICATIONS

Megyesi, M. et al. Highly sensitive fluorescence response to inclusion complex formation of berbertine alkaloid with cucurbit[7]uril, Feb. 9, 2008, Journal of Physical Chemistry C, vol. 112, pp. 3410-3416.*

Torr Canada, Droplet size distribution measurement apparatus, 2006, PTAC—2006 Water Innovation in the Oil Patch Conference.*

Oliveira M E C D R et al., "Solvatochromic Fluorescent Probes in Bicontinuous Microemulsions," Journal of Molecular Structure, Elsevier, Amsterdam, NL, vol. 563-564, May 28, 2001, pp. 443-447, XP007910443.

International Search Report in PCT/GB2009/001788.

Tyrie and Caudle, "Comparing Oil in Water Measurement Methods", Exploration & Production: The Oil and Gas Review 2007, Issue II, Nov. 2007, pp. 31-35.

Rurack et al., "A Highly Efficient Sensor Molecule Emitting in the Near Infrared (NIR): 3.5-distyryl-8-(p-dimethylaminophenyl)-difluoroboradiaza-s-indacene", New J. Chem, 2001, vol. 25, pp. 289-292, The Royal Society of Chemistry and The Centre National De La Recherche Scientifique.

Hogg, R., "Issues in Particle Size Analysis," KONA Powder and Particle Journal, No. 26 (2008), pp. 81-93, Hosokawa Powder Technology Foundation, Osaka, Japan.

Arthur, Daniel J. et al., "Technical Summary of Oil & Gas Produced Water Treatment Technologies," All Consulting, LLC, Tulsa, OK, Mar. 2005.

Benko, Katie L. et al., "Produced Water in the Western United States: Geographical Distribution, Occurrence, and Composition," U.S. Bureau of Reclamation, Environmental Science & Engineering Division, Denver, CO, Environmental Engineering Science, vol. 25, No. 2, 2008.

Ekins, Paul et al., "Management of Produced Water on Offshore Oil Installations: A Comparative Assessment Using Flow Analysis," Final Report, Mar. 2005, Policy Studies Institute, London, UK.

Igunnu, Ebenezer T., "Produced Water Treatment Technologies," International Journal of Low-Carbon Technologies, 2012, 1, 1-21, Oxford University Press, Oxford, UK.

Veil, John A. et al., A White Paper Describing Produced Water From Production of Crude Oil, Natural Gas, and Coal Bed Methane, Argonne National Laboratory, Jan. 2004, Argonne, IL.

Cusack, R. et al., "Rethink Your Liquid-Liquid Separations," Hydrocarbon Processing, Special Reports, Jun. 2009, pp. 53-60, Houston, TX.

* cited by examiner

METHOD TO ASSESS MULTIPHASE FLUID COMPOSITIONS

FIELD OF THE INVENTION

The invention relates to a method for assessment of a phase or an interface between phases in a multiphase sample, the multiphase sample containing an aqueous phase and an organic phase. More specifically, the invention relates to a method of assessment of various properties of a phase of the multiphase sample using a detection molecule that emits a signal when in contact with a phase of the multiphase sample. The invention further relates to the substances and systems used to carry out the method.

BACKGROUND OF THE INVENTION

Monitoring of oil in water is important for the oil production industry. One waste product of oil production is water, which is often injected to increase well pressure and maximise oil recovery. This produced water must be monitored before disposal, to avoid contamination of the disposal area with oil. As oil wells mature, they tend to produce greater volumes of wastewater. In many geographical regions the oil industry is regulated by legislation that dictates that the amount of oil disposed of in water waste products must not breach set levels. Improved monitoring of the quantity of oil in water could help the oil production companies to provide the required information for regulatory purposes. The companies could also use this information to monitor and maintain the efficiency of their equipment, and thereby reduce or avoid fines that could be incurred by breaching set levels.

Water treatment facilities would also benefit from improved methods of oil in water monitoring, because the quantity of oil in water can impact the efficiency of water treatment. By measuring and reducing the levels of oil in water, the efficiency of a variety of water treatments could be monitored, the operator can improve efficiency of treatment and better quality oil can be generated. If increased efficiency of water treatment can be demonstrated, an operator would be able to attract custom and cite environmental record as evidence for competency when tendering for new licenses. Furthermore, where the concentration of oil in the treated water is being regulated by legislation, a company could use improved oil in water monitoring methods to avoid fines and other legal action for breach of such legislation.

There are currently numerous methods available for oil in water monitoring: gravimetric methods, or direct weight measurement (for example US EPA Method 1664), colour of samples, infrared (IR) absorption, ultraviolet (UV) absorption, fluorescence and particle counting methods.

Gravimetric methods are advantageous in that they measure quantities of oil directly. However, the oil compounds that are assessed using such methods do not include all the organic compounds in the water being tested. Instead, the subset tested using gravimetric methods is made up of those compounds that are extractable from water in n-hexane at pH 2 and remain after the hexane is evaporated. Gravimetric methods are cumbersome and require a high level of manual skill, and as such cannot be used in most field environments.

Colorimetric methods were widely used before regulatory compliance was required, but are not applicable to many oils; firstly, because such methods may not generate sufficient colour to be visible within an oil sample, and secondly because the instrument is calibrated with a standard of known oil concentration. An instrument that has been calibrated in such a way has a standard background level of colour and is therefore only useful for experiments where the ratio of the oil components within the total volume of oil remains constant.

UV methods are based on the fact that aromatic compounds absorb UV radiation and fluoresce at different wavelengths. The amount of absorbed or fluoresced light is proportional to the concentration of aromatic compounds in the water. Extractions of fractions of the sample may or may not be used and can be useful in removing interferences e.g. iron, which can increase background fluorescence. UV absorption methods can be advantageously used for online monitoring, where extractions are not used as part of the method. Online monitoring has a number of advantages; no manual handling of the sample is required, there is an immediate response (<1 second) and the result can be correlated to a recognised standard reference method. One disadvantage of the system is that the absorption coefficient, or efficiency of light absorption, changes with the composition of the oil. Furthermore, UV absorption measurements are susceptible to interference. UV methods are, therefore, only accurate when the oil type and conditions are consistent. There are many situations in which these two factors are not consistent and monitoring may therefore not be reliable, for example; where two different reservoirs with different oil types are to be assessed, where scale has formed in the system, where dissolved oils are present, or where the concentration range is too great i.e. varies from low to high.

Fluorescence-based methods also suffer from difficulty in achieving a strong signal to background ratio. This is because different oil types and different water samples give different levels of background autofluorescence, so that it can be difficult to ascertain the signal from the hydrocarbon component of the sample. In addition, treatment chemicals such as corrosion inhibitors or solids encountered during oil production may interfere with signal generation or analysis. In both UV absorbance and UV fluorescence experiments, measurements made where the concentration of oil is low are affected by error due to the "stray light effect", and measurements made at higher concentrations of oil are subject to error from the "inner filter effect".

Methods using IR absorption to measure oil in water use detection of the carbon hydrogen (C—H) bond, which is common to almost all hydrocarbon compounds. The signal from the O—H bond in water overlaps the C—H signal so a liquid-liquid extraction of the oil with a solvent with no C—H bonds must be be performed prior to analysis. The extraction step is time-consuming, expensive and requires toxic chemicals. In addition to this, it remains controversial because some essential data may be lost using this technique due to the limited range of the IR spectrum that is analysed.

The most widely used approaches for monitoring of oil in water include gas chromatography with flame ionisation detection (GC-FID). GC-FID equipment is expensive, can be unreliable, has a limited dynamic range, requires an extraction step using solvents, uses pressurised gases, requires a heating oven, is not suitable for volatile mineral oil and carries some safety issues. It has been found that different lab personnel, equipment and procedures can produce significantly different results, so that reliable conclusions cannot be drawn from results. The equipment used for GC-FID is very large and therefore difficult to store; in particular, the equipment is not sufficiently robust for straightforward use at offshore sites and maintenance issues are common. The equipment becomes clogged easily, and the extraction step is time-consuming, requires skilled personnel and causes the loss of some fractions from the sample. GC-FID provides a method of off-line monitoring. This means that a sample is taken at, for example, an oilrig, and transferred to an offshore lab or, more commonly, flown or shipped to an on-shore site where it will be tested.

Using off-line methods, it is not possible to obtain real-time information about the levels of oil in water. The time taken to transport, prepare and test the sample results in a delay between sampling and obtaining the results. This is undesirable for both regulatory and environmental reasons because waste water is constantly being disposed of Therefore, if a sample reveals that the amount of oil in the waste water is too high, this oil may have already been released into the environment. The company may then be fined and may incur further legal penalties. It would be preferable to have a method that is simpler and faster, more accurate, robust and reproducible, could be performed on site and which could provide results in real time, allowing for continuous monitoring, immediate detection of process upsets, reduction in personnel cost, reduction in sample transport cost, reduction in lab cost and that minimises variation caused by personnel, equipment or protocols. The results could then be obtained very quickly and the oil production facility or water treatment facility processes altered to address the problem and prevent contaminating wastewater from entering the environment.

Some of the problems occurring due to the presence of oil in water are outlined above. The reverse situation, water contamination in oil, can also create difficulties for oil production or water treatment. Oil produced by individual companies is transported along pipelines to the shore. One such pipeline is the Forties pipeline in the North Sea. Production companies pay by volume to transport oil from their production facilities via the Forties pipeline to the shore and therefore it is preferable to transport pure oil, rather than oil including a quantity of water. Separators can be used to remove excess water from oil to reduce transportation costs. Further examples of problems caused by water in oil include loss of efficiency of lubricating oils that are used across a wide range of industries, problems with hydraulic systems, increased corrosion of system components, microbiological growth, accelerated metal fatigue and additive precipitation. Improved monitoring of water in oil therefore has many potential advantages in a range of fields, including the food and drink industry, the pharmaceutical industry and shipping.

Multiphase flow meters are used in the oil and gas industry, but the technology is not reliable if the proportion of oil and water in the pipe is variable and unknown. Therefore, it would be advantageous for operators of terminals and refineries if the relative oil to water content could be determined to enable such meters to be used.

IR absorption/transmission can be used for detecting and quantitatively assessing water contamination in oil. Such testing may be carried out offshore on a floating production storage and offloading vessel using IR absorption. Testing is performed on crude oil lines as well as oil and diesel tanks and contaminated bilge water. However, only a small part of the whole volume of the tank is available for testing and therefore results may not reflect the true composition of the total volume of oil. Although IR testing is suitable for off-shore testing, the analysis is prone to interferences and requires complicated sample preparation and regular maintenance and calibration.

Other methods currently used to assess the presence of water in samples of oil include centrifugation, distillation, colourimetric 'Karl Fischer' titration, and testing the electrical behaviour of a sample, such as resistivity and capacitance. However, these methods cannot cover the whole range of problems that relate to water in oil testing, because these problems require solutions that provide anywhere from 0-100% water cut. Technologies capable of improving accuracy, robustness, maintenance and cost and which are available for online monitoring would be advantageous.

In addition to monitoring total volumes of oil in water or water in oil, it is important to be able to monitor the size of the oil or water droplets. Therefore, in addition to the gravimetric, colourimetry, UV, IR and GC-FID methods of analysing the presence of oil in water, methods have been developed for the assessment of oil or particle size, volume and concentration in a sample. Particle numbers and size distribution can be assessed, for example by using a Coulter counter, turbidity can be measured, and size distribution and other characteristics of particles and phases can be visually recorded online. Image analysis may also be used to assess oil droplet size. This uses a microscope (or other magnification optics) to observe particles, a camera to take an image and software to calculate the size, volume and other properties of the particles. The size limit for detection using image analysis is approximately 2 μm diameter. Another method that can be used is light scattering. The relative strength of light scattered by the oil droplets as a function of the angle of scattering can be used to determine the size of the oil droplets. The limits of detection for such techniques are governed by the wavelength of the incident light, around 0.6 μm diameter where visible light is used. Laser diffraction methods can detect particles lower than 100 μm in size but relatively dilute and uncontaminated samples are required.

Using these methods and equipment, the size and volume of all oil droplets in a known volume of water can be calculated and summed to determine the oil concentration in the water. In addition, it is difficult for particle counting equipment to detect droplets of oil, so that the techniques are not very reliable, or accurate and the results of the analysis experiments suffer from low signal to background ratios. Machines and data processing techniques that are required to obtain the assessment of the phase in the sample are therefore complex and expensive. A further problem is that there are size limits for detection of oil droplets when image analysis is used; outside a known range (around 2 micron), image analysis equipment simply cannot detect oil droplets so that these methods cannot measure soluble oil concentrations. (Tyrie and Caudle 2007 *Comparing oil in water measurement methods* Touch briefings, pages 31-35.) Light scattering techniques cannot distinguish between spherical particles and nonspherical particles and therefore may generate inaccurate estimates on the amount of oil and droplet size distribution based on incorrect diameter measurements. The results obtained by light scattering can vary significantly as a result of variations in sample preparation and also as a result of how the samples are subsequently handled. In particular, the results may be affected by dust particles or gas bubbles, which will also scatter light and lead to false positives.

Mechanical separators are used to separate oil from water, most of them operating by gravitational means of separation by allowing settling of the oil droplets on the surface of the water. As a general rule, the larger the oil droplet size, the more efficient the separation will be. The performance of the mechanical separator is strongly affected, therefore, by the size of the oil droplets. The droplet size can be highly variable, from <25 micron to >150 micron diameter. An improved method for assessment of the size of oil droplets in water would have a number of applications. It would be useful to system operators, who wish to, for example, determine the efficiency of oil in water separation by mechanical separators. Separator system developers wishing to assess the effect of droplet size on the system would find it useful to be able to determine the size of droplets over a large range. Improved monitoring of the droplet size would also help companies to prevent clogging of production wells or oil lines, and also to minimise disposal of waste water which contains volumes of oil that breach regulated levels.

Improved monitoring of oil droplet size in water would also be useful in oilfields where the produced water is reinjected into the reservoir to increase the reservoir pressure and enhance the rate of oil production. Water that is injected in this way must not contain particles which will block the porous formation as this would prevent further flow in the reservoir. A system which could accurately determine particle size and the nature of the particles (oil, sand, gas etc) would provide useful information for an operator when controlling the quality of the produced water for re-injection.

Treatment additives are commonly used in the oil and gas industries to ensure integrity of the production facilities and also to maximise production of fluids. It is necessary to monitor the concentration of treatment substances to ensure that they remain effective. This monitoring process can, however, be labour-intensive and expensive. Furthermore, these treatment additives are subject to environmental legislation. Therefore, when the levels of treatment additives exceed specified levels, operators of oil processing and waste water treatment plants may incur fines or other penalties. Many of these additives, such as methanol, monoethylene glycol, scale inhibitors and low dosage hydrate inhibitors partition primarily to a single phase of a multiphase mixture. Others such as emulsifiers and demulsifiers are used to disperse or separate immiscible liquids such as oil and water and are commonly used in oil production. Chemicals that act as surfactants including corrosion inhibitors and asphaltene inhibitors may also create oil in water and water in oil emulsions that require monitoring. Many standard off-line tests are available, but do not tend to provide accurate, up-to-date data reflecting the concentration of treatment chemicals in a system and a method of inline monitoring of treatment additives would be very valuable.

Monitoring the distribution of treatment additives has a number of applications. Operators can ensure that minimum inhibitory concentrations can be used, reducing the risk of flow assurance and asset integrity problems. If problems are identified, operators can carry out preventative action to minimise the risks of production loss, for example the regularity of squeeze treatments could be increased. Treatment additives would only need to be added to a system when the concentration had dropped to the minimum effective concentration, thereby reducing waste that would otherwise occur if chemicals were added on a more arbitrary basis. Improved monitoring would provide quantitative evidence of treatment substance usage within the system, this evidence being useful for environmental monitoring and regulatory compliance. The results obtained by monitoring treatment additives could also be used to provide information on oil quality and to minimise the threats caused by the treatment additives used in, for example, hydrocarbon and wastewater processing facilities. Being able to monitor chemicals such as surfactants, asphaltenes, emulsifiers and demulsifiers could also help in development of new products as this monitoring could be used to pinpoint how effectively they can disperse or separate immiscible liquids and so identify better products. Monitoring droplet formation may also be useful in development of separators and other equipment.

Treatment chemicals such as emulsifiers and surfactants are also used in other industries including the food and drink industry, the pigments and inks industry, the cosmetics industry, the pharmaceutical industry, the consumer goods industry (such as the detergents industry), colloids for the nanotech industry, polymer production and liquid crystal characterisation. It would be advantageous for product development to improve the monitoring of the concentration (and droplet size, where necessary) of emulsifiers, demulsifiers and surfactants in these industries.

Hydrocarbon fingerprinting.

Hydrocarbon fingerprinting is used to determine the hydrocarbon components of samples based on, for example, chain length. This method is useful to determine the content, purity and quality of oil, and also to determine the source of oil in order to track a source of pollution, the contribution made by a specific oil well to export lines, or to identify barrels of stolen or diluted oil. Samples are analysed using high resolution capillary gas chromatography—mass spectrometry, a complex, highly specialised technique, or or near-infrared spectroscopy which is not robust to the presence of aqueous phase in the sample. It would be advantageous to have an improved, simplified method of identifying the different hydrocarbons present in the organic phase of an oil sample, that could be carried out off-shore.

As discussed above, there are numerous problems associated with the monitoring of oil in water or water in oil. In general, one of the greatest problems is that most methods require extraction. Often the sample must be extracted using hazardous chemicals such as Freon or pentane before it can be analysed. Extraction causes the loss of some fractions of a sample, and this is particularly the case for benzene, toluene, ethylbenzene, and xylene (BTEX) aromatic compounds, which are more soluble in water than other components. BTEX chemicals are the highly toxic, but their presence in oil or water is often missed because they are lost during solvent extraction of the sample from the main body of the multiphase substance to be tested. Extraction takes time, requires skilled operators, and creates disposal problems due to the chemicals used, and there is wide variability in extraction results obtained from different operators and laboratories.

For the purpose of the present application, a number of terms will now be defined. A "multiphase sample" is a sample containing both aqueous and organic phases. The multiphase sample may be a produced fluid from an oil, gas or water production, processing or treatment facility. Multiphase samples taken from oil, gas or water production facilities are highly variable in composition and may consist predominantly of an aqueous phase, with a smaller organic component, or predominantly of an organic phase, with a smaller aqueous component. The "organic phase" of a sample taken from an oil or gas production facility will typically contain a mixture of hydrocarbons such as alkanes, cycloalkanes and various aromatic hydrocarbons and non-metals such as nitrogen, oxygen and sulphur. The multiphase sample may also contain contaminants as well as treatment additives used during the production process. "Background sample" will be understood to mean all components of the sample that are not to be directly assessed when using the method of the invention. For example, when the user wishes to measure oil in water, the background sample comprises the aqueous phase and all other non-organic components. A "background signal" is any signal that may be emitted by the background sample at any stage during the method of the invention.

Further definitions will now be provided in relation to the type of monitoring that may be performed. An "off-line" system allows the user to take a sample from a system, and analyse it at a later stage. Such a system is useful if the equipment for analysis is located far from the location at which the sample is taken. It can also provide the user with a method for collecting samples taken at various time points and then analysing them to produce data showing composition relative to time. An "at-line" system allows the user to remove a sample from the system and analyse it on site. For example, the user could remove the sample with a syringe through a needle port, mix it with a detection molecule, mount on a microscope slide and analyse the signal. A portable spectrofluorometer may also be used for the detection step. This system is not real time but is rapid, and all of the equipment is portable and may be automated, making this method of testing suitable for offshore use. "Inline" methods involve analysing system components in situ in real time. An example might be the upstream injection of some dye, a mixing chamber and then snapshot imaging or fluorescence reading. Whilst it may be possible to achieve this in the main pipe (using the general flow of fluid to mix in the marker) it is much more likely (due to amounts of needed for such large volumes and ability to detect signal through wall) that any in-line system would require a loop (e.g. similar to those used currently for gas chromatography fast flow loops) to be drawn off the main flow but in such a way that it was representative. In this way it may be that we have a line that draws a representative fluid from the main line and into which marker is injected. This then feeds into a flow cell connected to fluorometer, imager etc. This line may rejoin the main flow or be removed to waste (depending on toxicity of marker, bioaccumulation risk of marker or volumes to be stored etc). An "online" system may be an automated monitoring system, which feeds directly into a computerised system for monitoring offsite. For example, an online system may incorporate an automated "in-line" system, information from the in-line system being recorded directly to the operator's computer system so that technicians at a different location may review it. This method advantageously allows data to be recorded in real time, but the personnel required to analyse the data would not need to be on-site.

SUMMARY OF THE INVENTION

It is an object of the present invention to address the problems highlighted hereinabove.

In a first embodiment of the invention, there is provided a method for the assessment of a multiphase sample, the multiphase sample comprising an aqueous phase and an organic phase, the method comprising:
a. adding at least one detection molecule to the multiphase sample to create a mixture containing the at least one detection molecule and the multiphase sample,
b. detecting a signal emitted from the mixture, the signal being detectably different when the at least one detection molecule is present in one of either an organic phase, an aqueous phase or an interface between said organic phase and said aqueous phase of the multiphase sample; and
c. analysing the detected signal to assess the properties of a phase or an interface between phases.

This method advantageously will allow the user to conveniently, directly and accurately assess a phase of a sample. Properties of the phase that could be assessed include the presence of oil droplets in water or water droplets in oil and relative proportions of phases. The data obtained as a result of analysing the signal could be advantageously used to determine such phase properties as, for example; droplet size, droplet shape, agglomeration state and composition. In addition, monitoring of an interface between two phases, or between one phase and a treatment chemical, is useful where the operator wishes to observe the boundary between oil and water within a vessel or a pipe. At least one dye that emits a signal from the interface between the two phases would provide a direct and simple way of visualising this boundary and thereby determining the relative proportions of both phases.

No solvent extraction step is required, so that the method will not require the use of toxic solvents or large volumes of flammable solvents that are typically required for such extraction steps. In addition, this method will also be faster than methods requiring extraction steps, reducing analysis time and minimising variability. Samples do not need to be monitored prior to disposal due to the absence of hazardous solvents. No highly trained operators are required for such a method. The method of assessing a phase of a multiphase sample could have further applications within many areas, such as the industries relating to food and drink, pharmaceuticals, pigments and inks, cosmetics and consumer goods such as detergents.

The sample may be taken from an oil, gas or water production, processing or treatment facility. The method has many particular advantages for use within the oil, gas and water industries. The method allows for direct monitoring because the presence of oil or water may be visualised by the presence of the signal emitted by the at least one detection molecule in contact with either the organic or aqueous phases respectively. In other words, the signal to background ratio can be enhanced because the at least one detection molecule will only emit a signal from the particular phase that is to be assessed.

It may be advantageous, depending on the at least one detection molecule selected, to irradiate the sample with electromagnetic radiation prior to detection of the signal. This will be the case where a signal is emitted by the at least one detection molecule after irradiation, for example a UV fluorescence signal. Adding this step enables a wide range of detection molecules to be used in the method of the present invention.

The sample may be subjected to ultrasonic sound waves prior to addition of the at least one detection molecule, after addition of the detection molecule but prior to detecting a signal emitted from the mixture or both prior to addition of the at least one detection molecule and after addition of the detection molecule but prior to detecting a signal emitted from the mixture. This process, known as sonication, would produce a sample with oil droplets (in water) or water droplets (in oil), the droplets being of uniform size. This method step would ensure that all droplets have the same surface area to volume ratio. This would have particular use where it is important to analyse the total volume of water in an oil sample or oil in a water sample, because the surface area from which a signal would be emitted by the at least one detection molecule would always be representative of a particular volume of droplet. This would reduce the need for the complicated image processing techniques that are normally required in light scattering and imaging methods.

Alternative method steps for ensuring that all droplets have the same surface area to volume ratio include the use of surfactants or shear forces (i.e. stirring or similar). As with sonication, this method step may be carried out prior to addition of the at least one detection molecule, after addition of the detection molecule but prior to detecting a signal emitted from the mixture or both prior to addition of the at least one detection molecule and after addition of the detection molecule but prior to detecting a signal emitted from the mixture.

The three method steps suitable for ensuring that all droplets have the same surface area to volume ratio may be used alone or in combination.

Preferably, the at least one detection molecule will disperse throughout the organic phase and aqueous phase of the multiphase sample and will emit a signal only on an interaction with one of the organic or the aqueous phase or the interface. It is advantageous to use a molecule that can disperse easily throughout the multiphase sample, so that it can interact with all volumes of both the organic and aqueous phases. This addresses the problem that the sample may contain small droplets of, for example, water within a volume of the organic phase. In such a case, a hydrophilic molecule may not reach the small droplets of water, because the surrounding organic fluid repels the hydrophilic molecule. The reverse is of course true; a hydrophobic molecule may not be able to reach small amounts of organic fluid, because it is repelled by the surrounding aqueous phase. In such a scenario, some volumes of the phase to be assessed may be 'hidden' from detection by the surrounding phase, so that measurements are inaccurate. One way of addressing this problem, would be to dissolve the at least one detection molecule in a small volume of an aqueous solvent, so that it may then reach the droplets of oil in the water. However, by doing this, the proportion of water in the sample is increased and this affects the results. This problem is avoided by the use of a detection molecule that is capable of dispersion throughout the multiphase sample, but which only emits a signal on interaction with a specific phase. Furthermore, the at least one detection molecule of this preferred feature of the invention is responsive to its surroundings. Using such a molecule, the presence of any target components of a mixture such as dissolved and dispersed oil, hydrocarbons of all chain lengths, and also the presence of additives such as monoethylene glycol, methanol and corrosion inhibitors could be assessed.

Preferably, the at least one detection molecule emits a detectable fluorescence change due to the difference in the induced dipole moment between the ground and excited states that results from the nature of molecules in its surrounding environment. Such detection molecules are highly sensitive to their surroundings; the polarity of the surrounding fluids alters the electronic energy gaps in the at least one detection molecule, so that the detectable fluorescence changes. Detection molecules with this feature therefore emit a different fluorescent signal depending on whether they are in an organic phase, an aqueous phase, or at an interface between an aqueous or organic phase. This provides the advantageous feature that a single detection molecule will emit signals at multiple different wavelengths, each signal corresponding to a discrete phase or interface between phases. The ability to differentiate different phases and interfaces between the phases is especially useful where treatment additives in a sample have caused emulsification of the phases to occur. For example, corrosion inhibitors may be amphiphilic and therefore can accumulate at interfaces between organic and aqueous phases. Therefore, they can surround a droplet of oil in aqueous surroundings, so that there is an interface between the corrosion inhibitor and water, and between the corrosion inhibitor and the oil. The induced dipole moment of the at least one detection molecule will be different at each interface and also in the oil and water phases of the sample. This preferred feature of the invention allows the user to very easily detect the interfaces and the phases, which is useful, for example, for detection of the presence of treatment chemicals as well as for detection of droplets of one phase within another phase.

The at least one detection molecule may be hydrophilic. A hydrophilic detection molecule will partition to the aqueous phase and emit a signal, which will enable the user to directly visualise the presence of water in the sample. Alternatively, the at least one detection molecule may be hydrophobic. A hydrophobic detection molecule will partition to the organic phase and emit a signal, which will enable the user to directly visualise the presence of oil in the sample. A large number of dye molecules naturally partition to one phase in a sample, and therefore these two features provide the user with a wide range of dyes that are suitable for use according to the invention. Two detection molecules, one of which is hydrphilic and one of which is hydrophobic, may also be used.

Preferably, the mixture will be processed so that the at least one detection molecule is dispersed throughout at least one phase of the multiphase sample before the signal detection step. As discussed above, it may be necessary to process the sample in order to ensure that the at least one detection molecule has been effectively dispersed throughout a phase of a multiphase sample. This is because, where there are droplets of one phase within a large volume of another phase, processing may be required in order to ensure that all of the droplets are available for interaction with the at least one detection molecule. This is particularly important where the proportions of different phases within a sample are to be accurately characterised. There are many methods known in the art for ensuring good mixing of substances and could include, for example, sonication or shaking.

The at least one detection molecule may interact with either the organic or aqueous phases or the interface between said organic and aqueous phases in a sample via hydrogen bonding, electrostatic interactions, Van der Waals forces, London forces, hydrophobic interactions or a combination thereof. These forces and bonds are sufficiently strong that they remain partitioned to the phase or the interface to be assessed for at least as long as is required in order to assess the properties of the phase or the interface.

Preferably, the signal is emitted at a wavelength of electromagnetic radiation that is different to that emitted from the background sample. By determining the electromagnetic radiation of a certain wavelength that is emitted by the at least one detection molecule, the user can determine simply and easily the presence of a phase. This may also be advantageous where the wavelength of the emitted signal is very far from the background signal from the phase that is not to be assessed; the signal to background ratio will be very strong, without requiring any complicated signal processing.

The signal may be measurable by a detectable change in the intensity of electromagnetic radiation from the mixture. For example, the at least one detection molecule may emit a signal that is more intense than that of the background signal from the phase that is not to be assessed. The user can therefore, by measuring the intensity of electromagnetic radiation before and after addition of the at least one detection molecule, detect the phase that is to be assessed. For example, oil is known to fluoresce. This can be a problem if an assay uses fluorescent markers to identify a component or contaminant in an oil sample, and complicated signal processing techniques may be needed to separate the fluorescence emitted by the marker from the fluorescence signal originating from the oil. It is possible, using a change in intensity of fluorescence, to separate the signal emitted by the phase of interest in the multiphase sample from the signal emitted by the background signal.

Preferably, the electromagnetic radiation is in the far red or IR spectrum. IR analysis is particularly advantageous for samples high in oil, because oil tends to autofluoresce at visible wavelengths. If the sample is excited using IR radiation, it is not necessary for the user to perform complicated signal processing techniques such as removal of background signal.

The signal may be measurable by a signal that has an electromagnetic radiation lifetime that is detectably different to a background signal. Optionally, the fluorescence lifetime characteristics of the signal emitted by the at least one detection molecule are detectably different to the fluorescence lifetime characteristics of a background signal. Modified difluoroboradiaza-s-indacenes, diethylthiatricarbo-cyanine iodide (DTTCI) and IR-125 have altered lifetimes depending on the hydrophobicity or polarity of the environment. This method provides the advantage that the fluorescence can be monitored over time, and the data resulting from a fluorescent signal with the expected lifetime for the at least one detection molecule can be used to identify and assess the phase of interest. Furthermore, if the fluorescence lifetime of the at least one detection molecule is greater than the fluorescence lifetime of the background signal, the user can allow the background signal to dim, so that only the signal from the at least one detection molecule remains. It is then simple to measure the signal emitted by the phase of interest in the multiphase sample.

Preferably, the fluorescence polarisation characteristics are measurably different to the fluorescence polarisation characteristics of a background signal. Fluorescence polarisation is easy to detect and therefore provides a simple method for assessing the properties of the phase of interest. It is simple to separate the signal emitted by the phase of interest in the multiphase sample from the signal emitted by the other, background phase of the multiphase sample, for example from autofluorescence of oil.

The signal may be a change in colour. This is particularly useful where a sample is colourless or has only a very weak colour, and therefore a change is easily detectable and indicative of the presence of a particular phase.

A property of at least one of the phases may be altered to enhance detection of the phase. Where a signal emitted by a detection molecule is weak, this technique could be advantageously used in order to enhance the signal to a detectable level.

The pH of the phase may be altered by addition of acid or base and the signal emitted by the at least one detection molecule is enhanced due to the acidic or basic nature of the phase. For example, the user may add such an aqueous soluble acid in order to acidify the aqueous phase. An aqueous dye, which fluoresces optimally in an acid environment could then be used as a detection molecule. The organic phase of the mixture might be similarly altered. This would advantageously allow the user to select pH-responsive dyes or makers in order to identify a particular phase.

The relative solubility of the at least one detection molecule might be altered by using host-guest chemistry to introduce the at least one detection molecule in to the target phase of interest. For example, the at least one detection molecule could be dissolved in a cyclodextrin solution and captured within its core as a non-covalent complex. The host-guest complex could then be added to the target analyte and dissolve within the phase of interest where the target molecule would not normally be soluble. The at least one detection molecule may then be detected by some physical, chemical, optical or electrical means.

The at least one detection molecule may be at least one dye. Dyes are widely available, well characterised and easy to use without significant expenditure on equipment or training of personnel. Preferably, the dye is a solvatochromatic dye. Such dyes advantageously emit a signal with measurably different spectral characteristics, depending on the nature of the surrounding environment such as length of the hydrocarbon chain present. The induced dipole moment of dyes is altered by the polarity of the surroundings. Oil has a lower polarity than water, so that different phases, or the interfaces between the different phases, will induce a change in the energy bands of the dye molecule. By using a single dye, a number of different components and/or properties of a single phase may be assessed.

Preferably, a wide range of wavelengths of the signal emitted by the dye is detected and analysed. As the signal is being emitted by a solvatochromatic dye, this data may be used to identify several properties and/or components of a single phase of a multiphase sample. This may have particular advantage for producing a 'hydrocarbon fingerprint' of a sample. For example, a detection molecule may emit a signal of a different wavelength, depending on the length of the chain or aromaticity of the hydrocarbon with which it is interacting. Scanning the sample across a wide range of wavelengths would therefore produce a signal 'fingerprint' that is specific to the composition of the sample being assessed.

Preferably, the method of the invention is used to detect and measure the concentration of treatment chemicals. The use of a solvatochromatic dye according to this feature can also be used to detect and analyse other components in the phase. For example, methanol, monoethylene glycol, scale inhibitors and low dosage hydrate inhibitors partition to a single phase of a multiphase mixture. Therefore, a solvatochromatic dye that is specific to a certain phase can be used according to the invention to assess the presence, concentration and dispersal of such treatment chemicals within a phase of the sample. The solvatochromatic dye may be hydrophobic, hydrophilic or may disperse easily in both organic and aqueous phases. The signal that would be obtained using such a method would appear as a 'fingerprint' as described above in relation to hydrocarbon fingerprinting, in which each treatment chemical and hydrocarbon would result in a specific signal on interaction with the at least one detection molecule. A calibration curve of the signal emitted by solutions of treatment chemical at different concentrations would be produced, and the signal emitted by the multiphase sample compared to this. Such a method may require chemometric methods, such as principle component analysis or multi-variate curve analysis, in order to extract the required components of data from the emitted signal, so that the concentration of the treatment chemical can be ascertained.

Preferably, the dye is selected from phenoxazone dyes, carbocyanines, and pyridinium betaine dyes. These dyes are soluble in organic and aqueous phases (and therefore are capable of dispersion throughout a multiphase sample), have low limits of detection, limited photobleaching and are stable under the extreme conditions of temperature and pressure that are commonly found in oil, gas and water processing and treatment facilities.

In addition, such dye molecules are useful for the purpose of assessing the target components of a sample taken from or within an oil, gas or water processing system because they can be effective even at the extreme conditions encountered in oil production or water treatment, for example high temperatures (e.g. 100° C.) and high pressures. Such detection molecules are also effective for detecting oil in water or water in oil at the detection range of 0 to 100 ppm, with an accuracy of ±10% and 4 ppm resolution.

Preferably, the at least one detection molecule is Nile Red. Nile Red is ideal for assessment of the organic phase of a multiphase sample, because it will emit a more intense signal on contact with the organic phase than on contact with the aqueous phase. Additionally, it has strong photochemical stability, an intense fluorescence emission peak, good solvatochromatic properties, is inexpensive, is very stable in highly concentrated acids, and its fluorescence emission spectrum does not lie within the region of chlorophyll autofluorescence and light crude oil (condensate) autofluorescence, so interference from algae and certain oils is minimised. It has also been shown that Nile Red emits a different fluorescent signal when it is in the presence of corrosion inhibitors, oil, or water.

Preferably, two different detection molecules will be introduced to the analyte sample where one molecule is capable of performing Fluorescence Resonance Energy Transfer (FRET) with the other. A set of two such molecules is commonly known as a "FRET pair". The FRET technique has the advantage of determining the localisation of one molecule in relation to the other and so can show regions of interface or mixing between the two. FRET technology is well understood and could allow a user to detect molecules of an analyte.

The method of the present invention may be used to assess the volume of a phase in the multiphase sample. The proportionate or total volume of either the organic phase or the aqueous phase in the multiphase sample may therefore be determined without the disadvantages of the prior art methods as discussed hereinabove, for example the need for the cumbersome equipment and complicated methods required in GC-FID.

The method may be used to determine the size distribution of droplets of either the organic phase or the aqueous phase in the multiphase sample. Known methods of particle counting of image analysis could be used so that the user can apply this method for a simple method of assessing the size of droplets of a phase. The feature of using a detection molecule will increase the detectability of droplets of smaller sizes, because the signal emitted from the phase of interest will be enhanced. The signal to background ratio will be improved so that no expensive or complicated signal processing is required.

The concentration of the at least one detection molecule, and the consequent proximity to and interaction with an other detection molecule causes a change in signal intensity or wavelength. This signal can be used to determine the amount of a particular phase present in the multiphase sample. This includes dyes which self-quench, that is a dye which does not efficiently fluoresce when in close proximity to one or more identical molecules but will fluoresce in more dilute solutions when the neighbouring identical molecule is at a longer than average distance. Preferably, the at least one detection molecule and the other detection molecule are two members of a FRET pair.

In methods in which the sample is irradiated with electromagnetic radiation prior to detection of the signal, the electromagnetic radiation may be provided by a laser, an LED or a flashlamp. The detector may be a fluorescence detector, luminometer, optical microscope, photomultiplier tube (PMT), charge coupled device (CCD) camera, complementary metal oxide semi-conductor (CMOS) camera, charge injection device (CID) camera, photographic film, fibre optic device, photometric detector, micro electro mechanical sensor (MEMS) device, single photon detector, spectrophotometer, fluorometer, chromatography system or by eye. Online or at-line monitoring is made possible because no cumbersome equipment is required; the equipment that is used for the method of the invention is reliable and can be transported to off-shore locations. These advantages are especially relevant to the oil, gas and water industries because they are often positioned at difficult-to-reach or remote locations and therefore a method of on-site monitoring is more convenient.

The phase or the interface between phases may be assessed in-line. An in-line system could involve the use of a loop diverting a small but representative sample volume of fluid from the main flow. A detection molecule would be injected into the loop, the sample could then feed into a flow cell and the signal be detected by, for example, a snapshot imager or by fluorescence reading. An in-line system would advantageously provide the user with real-time data reflecting the composition of the multiphase sample.

The phase or the interface between phases may be assessed off-line. An off-line system advantageously allows the user to take a sample from a system, and analyse it at a later stage. Such a system is useful where a sample has been taken from an off-shore oil rig, and the oil rig has become too hazardous for carrying out assessment of the sample. In such cases, the equipment and personnel for analysis of the sample may be located far from the location at which the sample is taken.

The phase or the interface between phases may be assessed at-line. An at-line system allows the user to remove a sample from the system and analyse it on site. A portable spectrofluorometer may be used for the detection step. This system is not real time but is rapid, and all of the equipment is portable and may be automated, making this method of testing suitable for offshore use.

The phase or the interface between phases may be assessed online. An online system may be an automated monitoring system, which feeds directly into a computerised system for monitoring offsite. For example, an online system may incorporate an automated in-line system, information from the in-line system being recorded directly to the operator's computer system so that technicians at a different location may review it. This method advantageously allows data to be recorded in real time, but the personnel required to analyse the data would not need to be on-site.

A combination of one or more in-line, off-line, at-line and online assesments may be used to analyse the multiphase sample.

Preferably, the at least one detection molecule is non-toxic. This is particularly important because of environmental legislation relating to disposal of chemicals. If the at least one detection molecule is non-toxic, then operators will not need to be concerned with monitoring the at least one detection molecule in the sample before disposal.

Preferably, the at least one detection molecule is stable for at least one month. The storage conditions for chemicals may be ambient or may be defined by the manufacturer; in either case, such conditions are well known to the person skilled in the art. This will be useful for offshore operators, so that the at least one detection molecule can be delivered to the site and stored for extended periods of time. The at least one detection molecule will preferably be stable for three, four, five, six, seven, eight, nine, ten, eleven or twelve months and even more preferably will be stable for longer than this. The longer the period that the at least one detection molecule can be stored for, the more useful it will be for operators of remote facilities, because fewer deliveries of chemicals will need to be made.

In a second embodiment of the invention, there is provided a system for use in a method for the assessment of a multiphase sample according to the present invention, said system comprising:
  a. containment means for mixing at least one detection molecule with a multiphase sample;
  b. a detector focussed on the containment means;
  c. means to analyse the data collected by the detector; and
  d. means of transferring the analysed data to a central data repository or an operator This system is easy to assemble, fast and simple to use and the combination of features are therefore especially useful for use in the oil, gas and water industries, where locations are often remote or offshore.

The system may further comprise an electromagnetic radiation source focussed on the containment means. Preferably, the source of electromagnetic radiation is a laser, LED or flashlamp.

Preferably, the detector is adapted to detect emitted signals across a wide range of wavelengths. This will advantageously allow the user to compile a complete body of data relating to the signals emitted by the at least one detection molecule, which could for example be used to produce a hydrocarbon 'fingerprint'.

Preferably, the system will also include means for adding a substance for altering the properties of one phase of the multiphase sample. This feature will conveniently allow the user to add the substance directly to the multiphase sample before addition of the at least one detection molecule.

Preferably, the system comprises antifouling means. The antifouling means may one or more of sapphire windows, means for sonication of the sample, coatings on surfaces (e.g. the surfaces between the excitation source and the detector), a free flowing non-contact system in which the stream of fluid does not contact a surface or window but is detected directly, a system using a surfactant to clean contacting areas of the fluid stream, and an automated cleaning system (e.g. a system that wipes debris from a window, similar to windscreen wipers). Such means are well known in the art and are discussed, for example, in U.S. Pat. No. 5,185,531. These means will ensure that the signal emitted by the at least one detection molecule is transferred to the detector without distortion or reduction in intensity. The data obtained by the user will therefore reflect accurately the signal emitted and thereby the properties of the phase being assessed.

Preferably, the system includes means to raise an alarm where detected levels of the phase of interest have risen above specified levels. This provides a convenient and instant indication to the user, without any requirements for further analysis, that levels of a particular phase, for example, oil in produced water, have exceeded the desirable level. The user may then take appropriate action more swiftly than if he had been required to assess the levels himself. In this particular example, avoiding the disposal of water containing too much oil could help the company to avoid fines or other sanctions.

The system will preferably include means for safe disposal of the sample. This will provide the operator with convenient solution to the problem of waste disposal, in particular where toxic chemicals are used.

The system will preferably comprise means for reinjection of the sample back into the bulk flow of the system. The user has the advantage therefore that he does not need to consider waste disposal issues. This is especially useful for operators of offshore or remote sites, where it may not be possible to dispose of samples into the surrounding environment.

Preferably, the detector is a fluorescence detector, optical microscope, charge coupled device
(CCD) camera, complementary metal oxide semiconductor (CMOS) camera, charged injection device (CID), photographic film, fibre-optic device, photometric detector, MEMS device, single photon detector, spectrophotometer, spectrofluoro-meter, luminometer, system or eye. These are simple pieces of equipment, do not require skilled personnel, and provide results quickly and cheaply.

Preferably, the system is adapted to be portable. This is particularly advantageous because the operator may wish to conduct at-line, on-line or in-line assessments of a fluid, which may involve detection and analysis off-shore or at remote locations.

In a third embodiment of the invention, there is provided use of at least one detection molecule for assessment of a multiphase sample according to the method of the present invention, the at least one detection molecule being selected from phenoxazone dyes; carbocyanines; pyridinium betaine dyes; lipophilic carbocyanines: 1,1'-dioctadecyl-3,3,3',3'-tetramethylindocarbocyanine perchlorate (DiI), 3,3'-dioctadecyloxacarbocyanine perchlorate (DiO), 1,1'-dioctadecyl-3,3,3',3'-tetramethylindo-dicarbocyanine perchlorate (DiD), 1,1'-dioctadecyl-3,3,3',3'-tetramethylindotricarbocyanine iodide (DiR) and their derivatives; 1,6-diphenyl-1,3,5-hexatriene (DPH); trimethylammonium-DPH (TMA-DPH); 2-anilino-naphthalene-6-sulfonic acid (2,6-ANS) or bis-ANS; laurdan; 3,3'-dipentyloxacarbocyanine iodide ($DiOC_5$) and 3,3'-dihexyloxacarbocyanine iodide ($DiOC_6$); Invitrogen FM dyes 1-43, 4-64; Invitrogen dye RH 414 and NanoOrange reagent; disodium salt of 4-amino-4'-benzamidostilbene-2,2'-disulfonic acid (MBDS or BADS), diethylthiatricarbocyanine iodide (DTTCI); 4,5-benzoindotricarbocyanine (IR-125); N,N-dimethylamino-benzonitrile (DMABN); nitrobenzoxadiazole (NBD) labelled phospho-choline; octadecyl rhodamine B; benzophenoxazine-2-one (also known as nile red or nile blue oxazone); merocyanine 540; 4-(4-(pentadecylamino)styryl-N-methylpyridinium iodide (di-15-ASP); 3,3'-dihexadecylthia-dicarbocyanine iodide (diSC16 (5)); octadecyl acridine orange; difluoroboradiaza-s-indacenes (commonly called boron-dipyrromethene dyes or BDPs) and derivatives with additional aromatic groups; heterocyclic moieties or electron donating groups (Rurack et al., New J. Chem., 2001, 25, 289-292); solvatochromatic dyes; symmetrical tricarbocyanine near IR dyes (consisting of heteroaromatic structures linked by a polymethine chain containing conjugated carbon/carbon bonds); rylenes; squaraines; squaraine-rotaxanes; difluoroboradiaza-s-indacenes and quantum dots.

In a fourth embodiment of the invention, there is provided at least one detection molecule for use in the detection of an aqueous phase according to the method of the present invention, the at least one detection molecule being selected from fluorescein; Oregon Green; Cascade Blue; lucifer yellow; Auramine O; tetramethylrhodamine; pysranine; boron dipyrromethene difluoride (BODIPY FL); Sulforhodamines; Hydroxycoumarins; Polysulfonated Pyrenes; Cyanines; DyLights (Thermo Fisher Scientific); HiLytes (AnaSpec); AlexaFluor hydrazindes; Alexa Fluor 633 hydrazide; Alexa Fluor 647 hydrazide; and Alexa Fluor 647 hydroxylamine (Invitrogen); hydroxylamines; maleimides (Invitrogen); solvatochromatic dyes; neutral red or acridine orange; Polysulfonated Pyrenes such as 8-hydroxypyrene-1,3,6-trisulfonic acid (HPTS, also known as pyranine); Lysosensor probes (Invitrogen); and Quantum dots.

In a fifth embodiment of the invention, there is provided at least one detection molecule for use in the method of the present invention, wherein the at least one detection molecule is dispersed throughout the organic phase and aqueous phase of the multiphase sample and will emit a signal only on an interaction with one of the organic phase, the aqueous phase or the interface, and wherein the at least one detection molecule is selected from phenoxazone dyes, carbocyanines and pyridinium betaine dyes. These dyes may advantageously disperse throughout the aqueous and organic phases of the multiphase sample.

In a sixth embodiment of the invention, there is provided a composition for use in assessment of a multiphase sample according to the invention, said composition comprising:
 a. a multiphase sample; and
 b. at least one detection molecule,
  wherein the at least one detection molecule is capable of emitting a signal, the signal being detectably different when the at least one detection molecule is present in one of either of an organic phase, an aqueous phase or an interface between said organic phase and said aqueous phase of the multiphase sample.

This composition is very useful for providing a mixture that can be directly examined and analysed in order to assess the properties of the phase being assessed. This can be carried out, as discussed hereinabove, either immediately on addition of the at least one detection molecule, or following processing and/or irradiation of the sample in order to induce the emission of a signal from the at least one detection molecule. The at least one detection molecule is particularly useful because it is capable of emitting a signal that enhances the detectability of the phase of interest. There is a great need, as discussed above, within the oil and gas industries for a simple and direct technique for monitoring phases within a multiphase sample.

The at least one detection molecule may be selected from phenoxazone dyes; carbocyanines; pyridinium betaine dyes; lipophilic carbocyanines DiI, DiO, DiD, DiR and their derivatives; DPH; TMA-DPH; 2,6-ANS or bis-ANS; laurdan; $DiOC_5$ and $DiOC_6$; Invitrogen FM dyes 1-43, 4-64; Invitrogen dye RH 414 and NanoOrange reagent; disodium salt of MBDS, DTTCI; IR-125; DMABN; NBD-labelled phosphocholine; octadecyl rhodamine B; benzophenoxazine-2-one (also known as nile red or nile blue oxazone); merocyanine 540; di-15-ASP; diSC16(5); octadecyl acridine orange; difluoroboradiaza-s-indacenes (commonly called boron-dipyrromethene dyes or BDPs) and derivatives with additional aromatic groups; heterocyclic moieties or electron donating groups (Rurack et al., New J. Chem., 2001, 25, 289-292); solvatochromatic dyes; symmetrical tricarbocyanine near IR dyes (consisting of heteroaromatic structures linked by a polymethine chain containing conjugated carbon/carbon bonds); rylenes; squaraines; squaraine-rotaxanes; difluoroboradiaza-s-indacenes and quantum dots. These dyes are soluble mainly in the organic phase of the multiphase sample and may be especially advantageous where it is desirable to use a dye that will disperse only through one phase of the multiphase sample to the exclusion of the remainder of the sample.

The at least one detection molecule may be selected from fluorescein; phenoxazone dyes; carbocyanines; pyridinium betaine dyes; Oregon Green; Cascade Blue; lucifer yellow; Auramine O; tetramethylrhodamine; pysranine; BODIPY FL; Sulforhodamines; Hydroxycoumarins; Polysulfonated Pyrenes; Cyanines; DyLights (Thermo Fisher Scientific); HiLytes (AnaSpec); AlexaFluor hydrazindes; Alexa Fluor 633 hydrazide; Alexa Fluor 647 hydrazide; and Alexa Fluor 647 hydroxylamine (Invitrogen); hydroxylamines; maleimides (Invitrogen); solvatochromatic dyes; neutral red or acridine orange; Polysulfonated Pyrenes such as HPTS; Lysosensor probes (Invitrogen). These dyes are soluble mainly in the aqueous phase of the multiphase sample and may be especially advantageous where it is desirable to use a dye that will disperse only through one phase of the multiphase sample to the exclusion of the remainder of the sample.

BRIEF DESCRIPTION OF THE DRAWINGS

The invention will now be described with reference to the following figures and experiments, in which.

DESCRIPTION OF PREFERRED EMBODIMENTS

Figure 1:
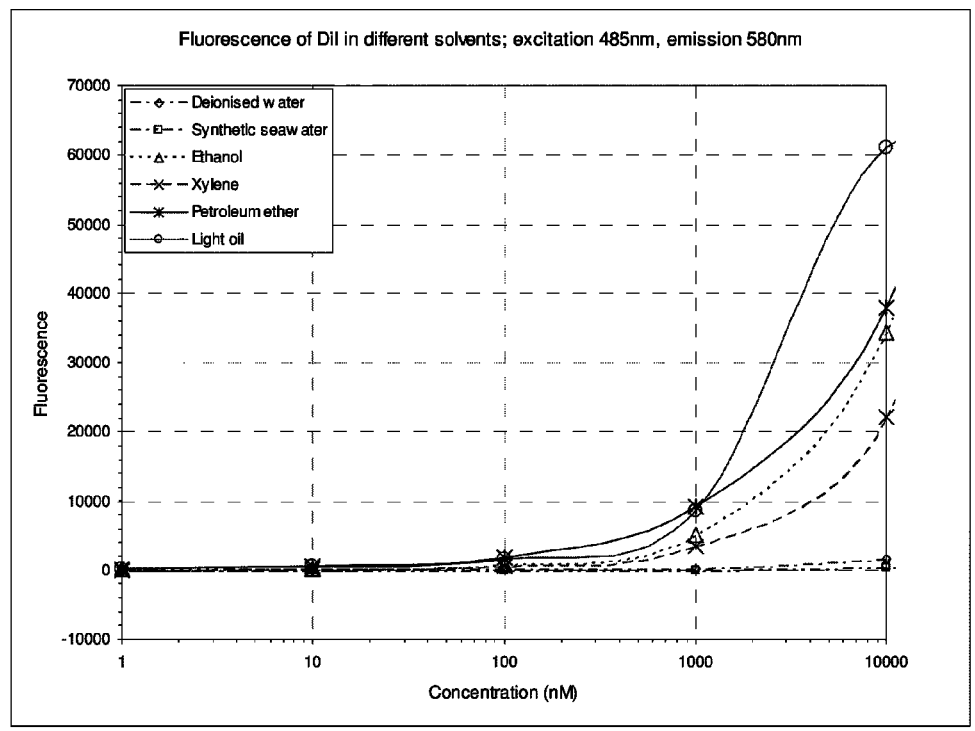
FIG. 1 is a graph showing the fluorescence of DiI in different solvents at 485 nm emission and 580 nm excitation.

1. Assessment of Various Dyes for Association with Organic Phases.

A user may select a detection molecule which fluoresces very brightly on contact with an organic phase, but which fluoresces extremely weakly, if at all, on contact with an aqueous phase. Of course, the user may be interested in analysing the properties of the aqueous phase, in which case a detection molecule that emits a measurably different signal on contact with the aqueous phase would be selected. The characteristics that may change on interaction with a particular phase could include, for example, brightness, intensity, colour, signal duration, excitation or emission wavelength, and fluorescence polarisation or fluorescence lifetime.

Where the user wishes to use changes in wavelength as a detectable signal, detection molecules could be selected which have large Stokes shifts, emission wavelengths, absorption efficiencies or emission lifetimes that are far from those of the test fluid. For example, when using an oil in water sample, a fluorescent dye that emits light on contact with oil in the IR, away from the most intense fluorescence of oil, may be used. As an additional example, when using a water in oil sample, a fluorescent dye that emits light on contact with water in the IR, away from the most intense fluorescence of the oil may be used.

Alternatively some pyrene dyes form excimers (excited state dimers) in high concentrations which emit red-shifted fluorescence but when concentration is reduced due to dilution of the dye, for example in larger oil droplets, excimer emission is replaced by blue-shifted monomer fluorescence.

Some dyes that are suitable for dispersion throughout both the organic and aqueous phases of a multiphase sample are phenoxazone dyes, carbocyanines, and pyridinium betaine dyes. These names each describe a chemical family that can be slightly altered to adjust the spectral properties. Many literature examples of these dyes describe molecules developed for life sciences uses, which have been prepared so that they can be added to aqueous solutions (so they are water soluble) but they stick to hydrophobic areas (such as cellular membranes) and are more fluorescent in that more organic environment. The actual ratio of amount of dye dissolved in the aqueous or the organic phase is governed by the particular "octanol-water coefficient" or "log P" which is a temperature-dependant constant for that particular molecule. In general, the phenoxazone dyes, carbocyanines, and pyridinium betaine dye families would be more associated with the organic than the aqueous phase. These dyes have never been used within the context of the oil, gas and water production, processing and treatment industries.

Specific examples of dyes whose fluorescence is enhanced in the organic phase versus aqueous include the lipophilic carbocyanines DiI, DiO, DiD, DiR and their derivatives; DPH; TMA-DPH; 2,6-ANS or bis-ANS; laurdan; $DiOC_5$ and $DiOC_6$; Invitrogen FM dyes 1-43, 4-64; Invitrogen dye RH 414 and NanoOrange reagent; disodium salt of MBDS; DTTCI; IR-125; DMABN; NBD-labelled phosphocholine; Octadecyl rhodamine B; benzophenoxazine-2-one (also known as Nile Red or nile blue oxazone); merocyanine 540, di-15-ASP, diSC16(5), octadecyl acridine orange; difluoroboradiaza-s-indacenes (commonly called boron-dipyrromethene dyes or BDPs) and derivatives with additional aromatic groups, heterocyclic moieties or electron donating groups (Rurack et al., New J. Chem., 2001, 25, 289-292), symmetrical tricarbocyanine near IR dyes which consist of heteroaromatic structures linked by a polymethine chain containing conjugated carbon/carbon bonds dyes, rylenes, squaraines and squaraine-rotaxanes. Where changes in fluorescent lifetime are used as a signal modified difluoroboradiaza-s-indacenes, DTTCI and IR-125 may be used as they have altered lifetimes depending on the hydrophobicity or polarity of the environment. Enhancement of signal may be related to the polarity of the different phases and other dyes, which fluoresce in nonpolar solutions, may be used for detection of oil in water. Octadecyl rhodamine B associates with lipid membranes and self-quenches at high concentrations. When the size of a droplet including octadecyl rhodamine B increases in size, the concentration of the dye drops, quenching is prevented and a fluorescent signal generated. Therefore this dye can act as an indicator of increasing size of droplets of an organic phase.

In order to assess a number of different dyes for use in detection of an organic phase, 1,8-ANS, Nile Red and DiI were added to a variety of pure solvents. The solvents assessed were deionised water, synthetic sea water, ethanol, xylene, (as a 10% solution in ethanol), petroleum ether and light oil. All dyes were shown to be soluble in ethanol and concentrated stocks made (0.5 or 1 mM). Plate fluorometry samples were analysed in black 96 well plates, using a Berhold Mithras luminometer (1 second read, 1000 lamp energy, normal aperture, top read). Cuvette fluorometery samples were analysed in disposable 1 cm path-length cuvettes, using a Picofluor™ hand-held cuvette-reading fluorometer, and the built-in protocols. For imaging, samples were pipetted onto microscope slides, a cover-slip added, and imaged using a fluorescence microscope, using either FITC or Rhodamine filter sets (FIG. 1).

At an excitation wavelength of 355 nm and an emission wavelength of 460 nm there was no relationship between 1,8-ANS fluorescence intensity and xylene or petroleum ether concentration. No further work was carried out with this dye.

At an excitation wavelength of 485 nm and an emission wavelength of 580 nm the fluorescence intensity of DiI increased with the concentration of petroleum ether. There was no impact on emission wavelength by the different solvents.

Figure 2:
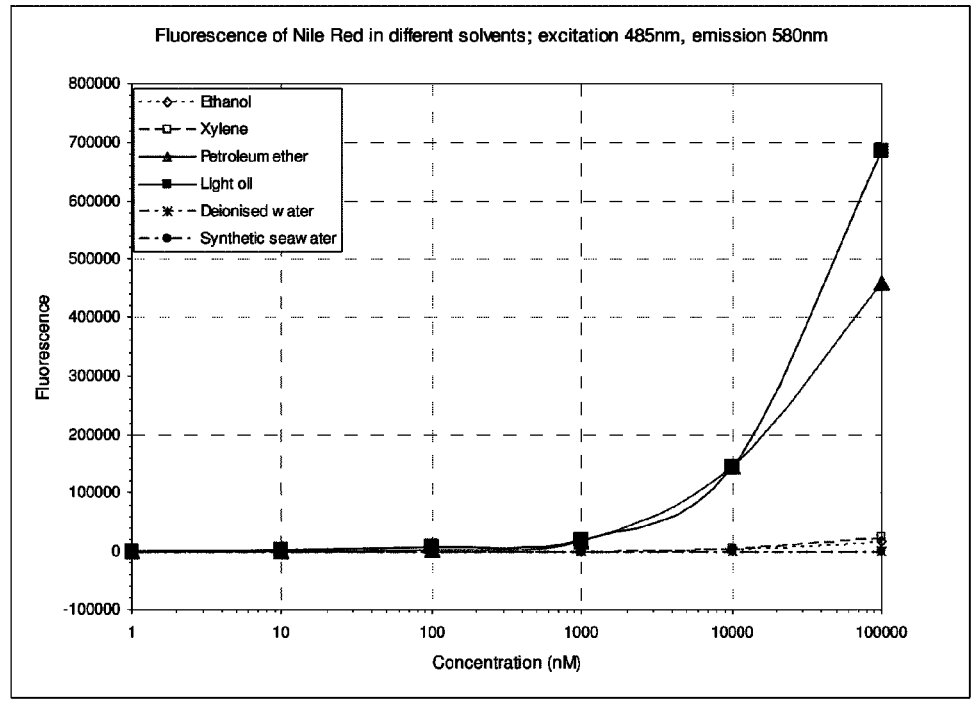
FIG. 2 is a graph showing the different fluorescence of Nile Red in different solvents at 485 nm emission and 580 nm excitation.

The fluorescence of Nile Red was very dependent on the solvent system. Using an excitation wavelength of 485 nm and an emission wavelength of 580 nm the limit of detection for Nile Red was 10 nM (3 ppb) in 100% light mineral oil (Baby oil; C-15 to C-40 typical chain length). Very little fluorescence from Nile Red was observed in aqueous systems (FIG. 2).

2. Solvatochromatic Nature of Dyes

Figure 3A:
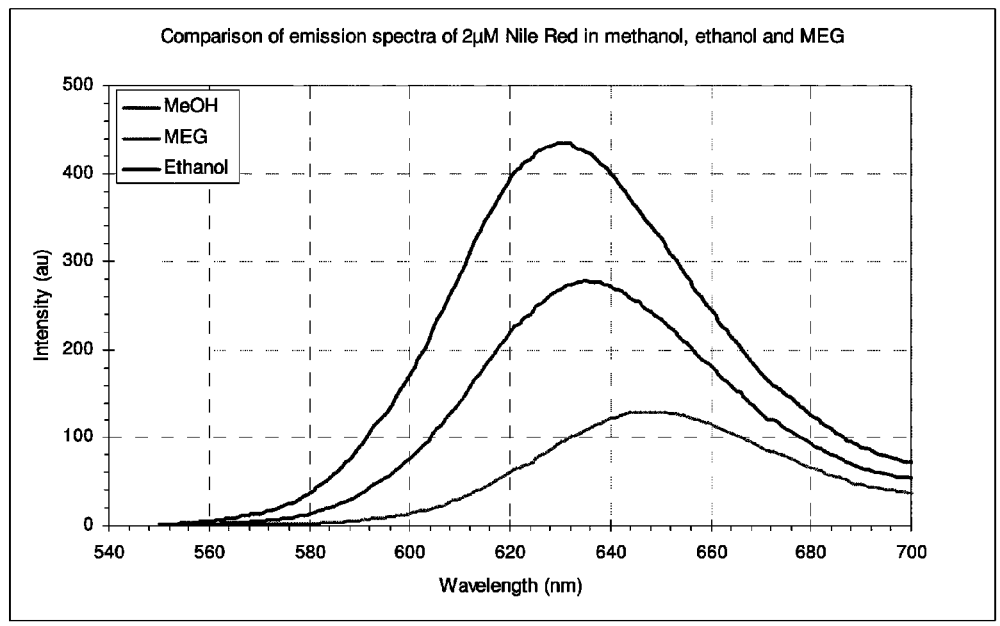
FIGS. 3A and 3B are graphs showing the different fluorescence emission spectra of Nile Red in different solvents; 3A in 100% methanol, ethanol or monoethylene glycol (MEG) at 485 nm excitation; and 3B in 100% petroleum ether, light mineral oil or xylene at 460 nm excitation.
Figure 3B:
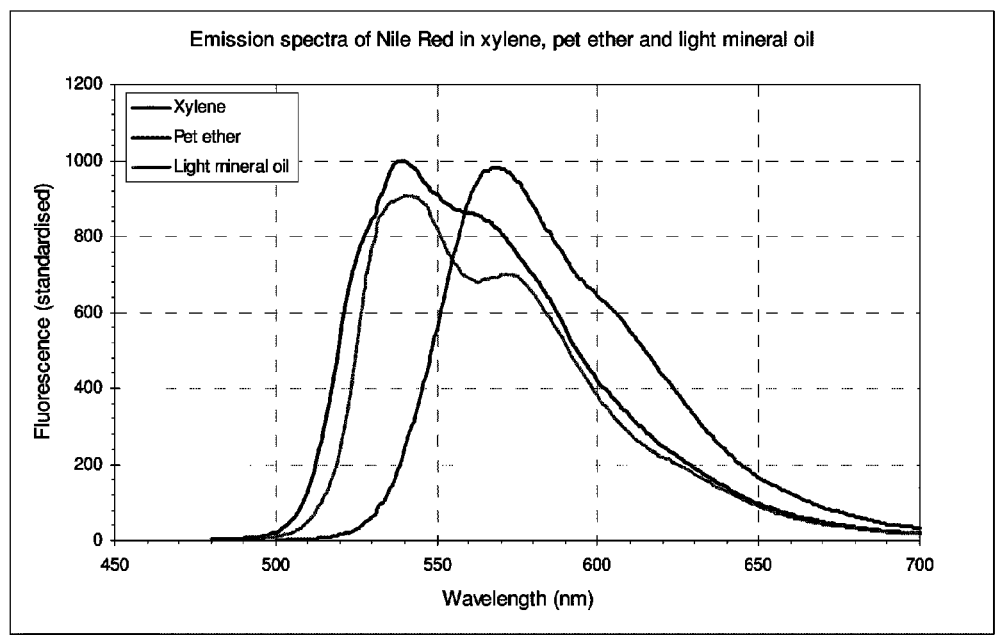
Figure 3C:
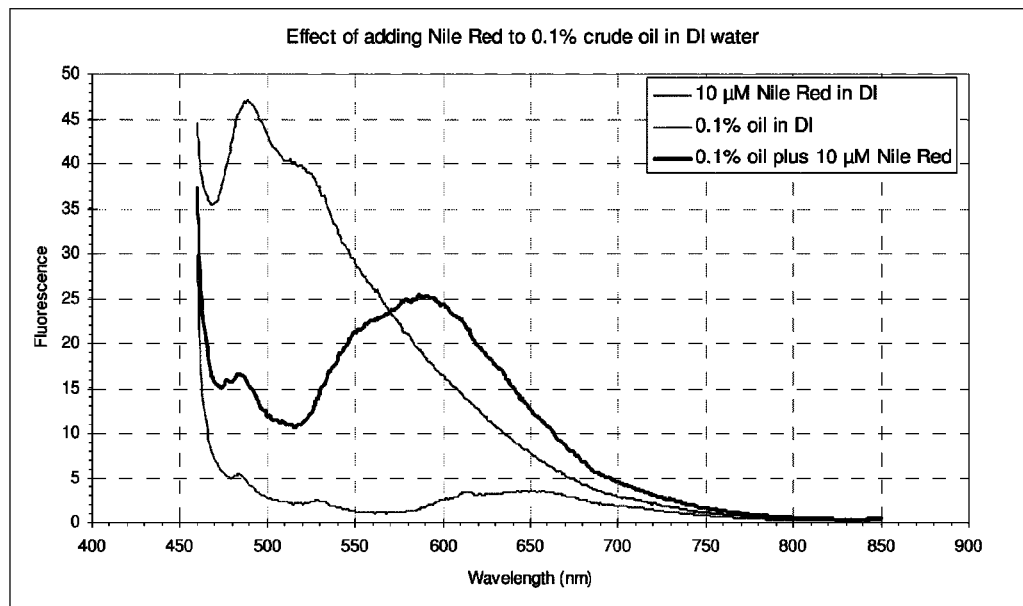
FIG. 3C is a graph showing the emission spectrum of 0.1% heavy crude oil in deionised water, 10 μM Nile Red in deionised water, and 10 μM Nile Red in deionised water containing 0.1% heavy crude oil; all at 450 nm excitation.

By eye it was clear that the wavelength of the emission was solvent dependent, i.e. solvatochromatic. This was confirmed by assessing emission and excitation using different filter sets (data not shown). In further work using a Varian Cary Eclipse scanning spectrofluorometer different spectra were observed for dye added to methanol, ethanol, monoethylene glycol, xylene and light mineral oil (FIGS. 3a and 3b). No difference was observed between light mineral oil and petroleum ether. This difference in spectra may be used to determine the content of any sample e.g. the proportion of different oil types or additives such as methanol, monoethylene glycol and corrosion inhibitors all of which produced different spectra.

3. Limits of Detection of Various Solvents

Figure 4:
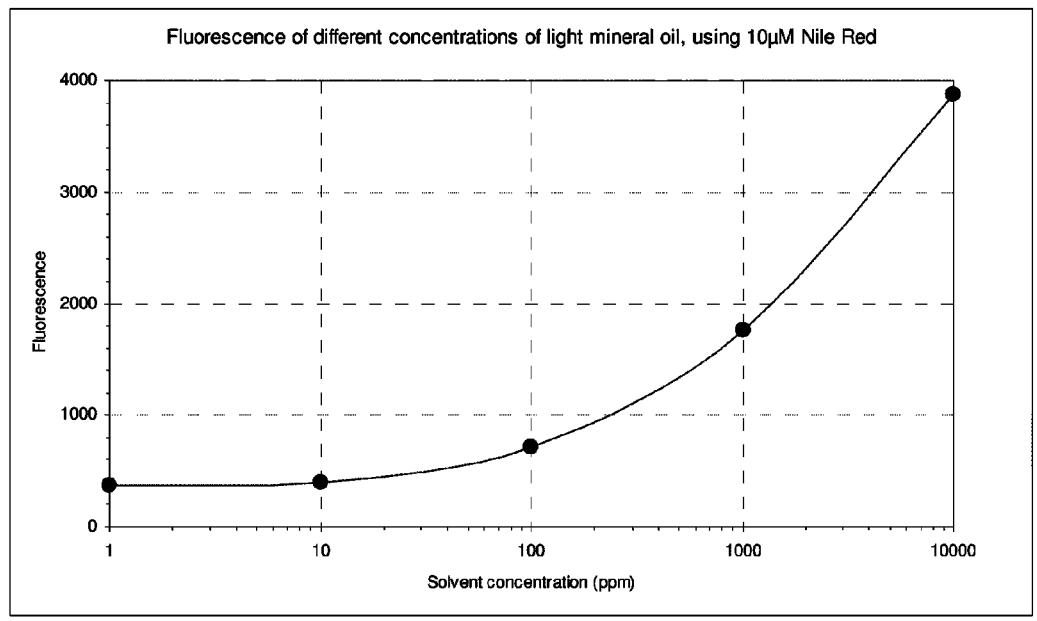
FIG. 4 is a graph showing the limits of detection of light mineral oil when using 10 μM Nile Red and a spectrofluorometry approach.

Assessment of the limits of detection indicate that this varies between solvents. For light mineral oil, using 10 μM Nile Red limits of detection <20 ppm were possible (FIG. 4). The value varied between different solvents.

4. Assessment of an Oil Sample Using Nile Red

Figure 5:
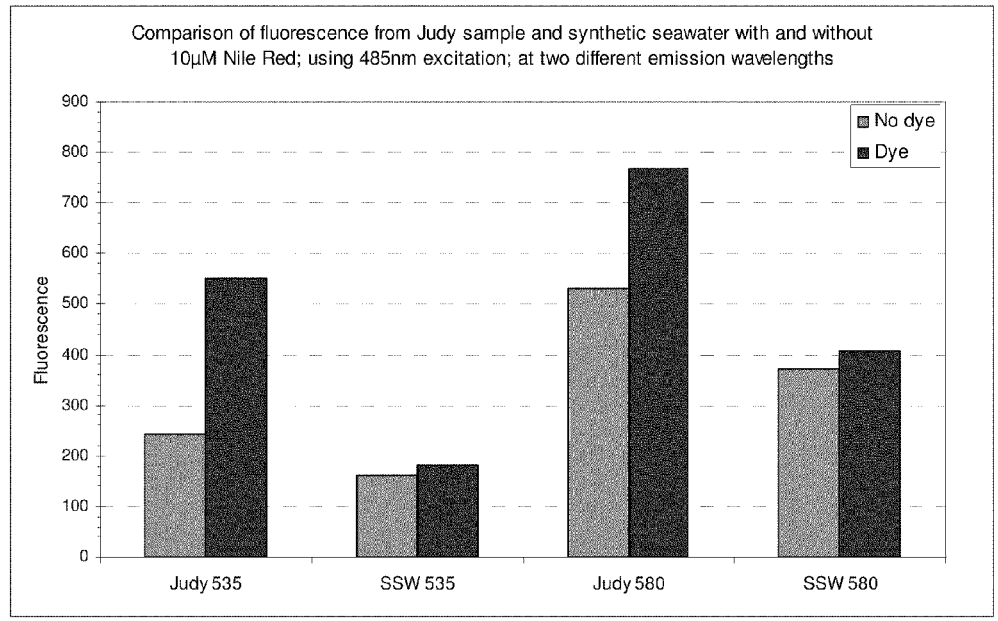
FIG. 5 is a graph showing comparisons between fluorescence of a 'Judy' oil-in-water sample with or without the addition of Nile Red.

A real oil in water sample was sourced from the Judy oilfield. The amount of oil present is not known. Addition of Nile Red to the sample (10 μM) caused a large increase in fluorescence of the real sample compared to synthetic seawater control indicating that oil was present and showing that the approach is applicable to real fluids (FIG. 5).

The highest potential oil level in a well will inform the quantity of dye that will be required. This would be determined as part of the installation qualification and the required volume would be written into the operating instructions as well as any other calibrations. For example, in order to determine the quantity of dye sufficient to accurately determine the properties of the phase of interest, the following procedure may be followed. Firstly, the historical levels of oil in water at a particular site would be reviewed and the average, maximum and minimum values calculated. Secondly, experiments would be conducted to determine how much dye must be added to accurately determine the maximum value of the quantity of oil in water. When it is used for determining the properties of a phase, the amount of dye used each time would be the same, ie the quantity required for detection and assessment of the maximum possible amount of oil in water—or even twice that much, if the operator so chooses. A calibration curve is determined for adding this amount of dye to a range of concentrations of oil in water and the calibration curve would be supplied at the time of installation at the particular site.

5. Assessment of an Oil Sample using Nile Red and Portable Equipment

Figure 6:
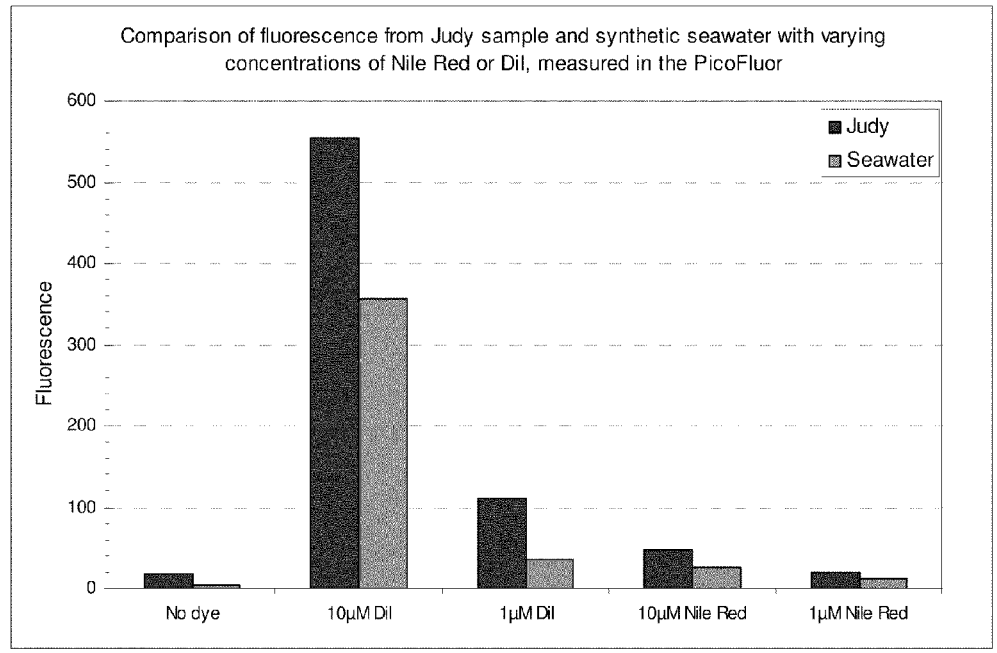
FIG. 6 is a graph comparing fluorescence of 'Judy' oil in water samples following addition of either Nile Red or DiI; measured using the Picofluor™ portable fluorometer.

A portable fluorometer (Picofluor™) was used to determine if the assay was transferable to equipment more suitable for use in the field. Again Judy samples were used and both Nile Red and DiI dyes tested. Similar results were obtained as previously although signal using DiI was greater than observed with Nile Red (FIG. 6), excitation 540 nm emission 570 nm. Optimisation of excitation and emission wavelength parameters is expected to further improve the assay.

6. Use of Image Analysis to Assess Oil Content with Nile Red Dye

Figure 7:
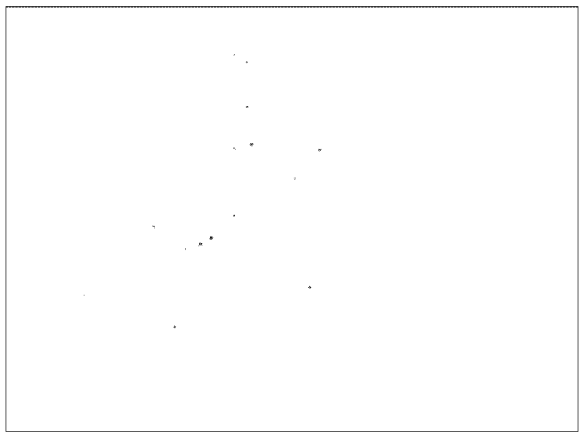
FIG. 7 shows dodecane oil droplets marked with Nile Red and fluorescing, the image was taken using a fluorescein isothiocyanate (FITC) filter set (485/535 ex/em) and the colours have been inverted.
Figure 8:
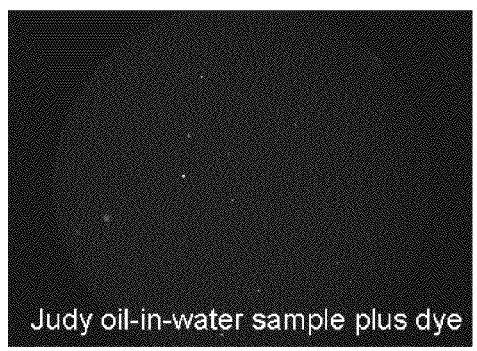
FIG. 8 shows images of droplets of water in oil, where the aqueous-soluble dye fluorescein was used to label the water droplets. Images were taken with a microscope with a FITC filter set (485/535 ex/em).
Figure 8:
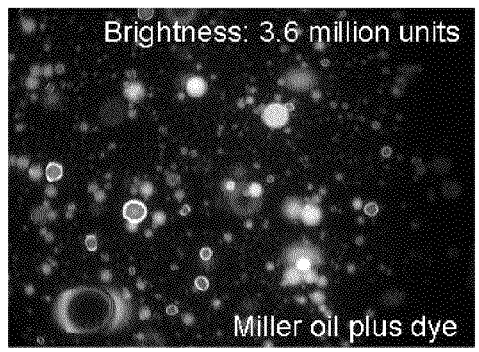
Figure 8:
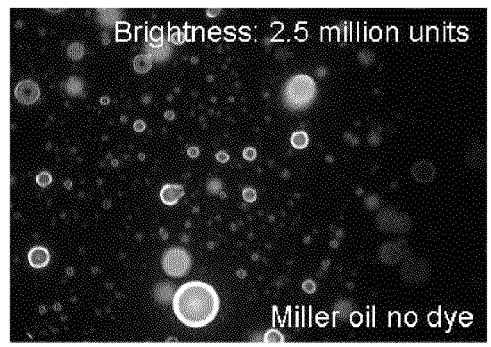

In addition to spectrofluorometry, details of the signal can be determined by imaging the samples. 10 μM Nile Red was added to varying concentrations of oil (dodecane) and imaged at 125× using a Nikon Fluorescent microscope. Clear images were obtained using both FITC (485/535 ex/em) and Rhodamine (540/605 ex/em) filter cubes (FIG. 7). Oil-in-water samples from Judy had limited background fluorescence and droplets were visible although oil taken from produced water (Miller field) at 0.1% dilution in deionised water showed significant background fluorescence in a similar region to Nile Red fluorescence. However, oil plus dye had significantly more fluorescence than oil alone (as determined using the integrated measure function of Image J to determine greyscale 'brightness', FIG. 8). In the field background fluorescence from oil may be subtracted or a dye used which fluoresces outwith the oil fluorescence e.g. emits in the IR.

7. Determination of Droplet Size Resolution

Figure 9:
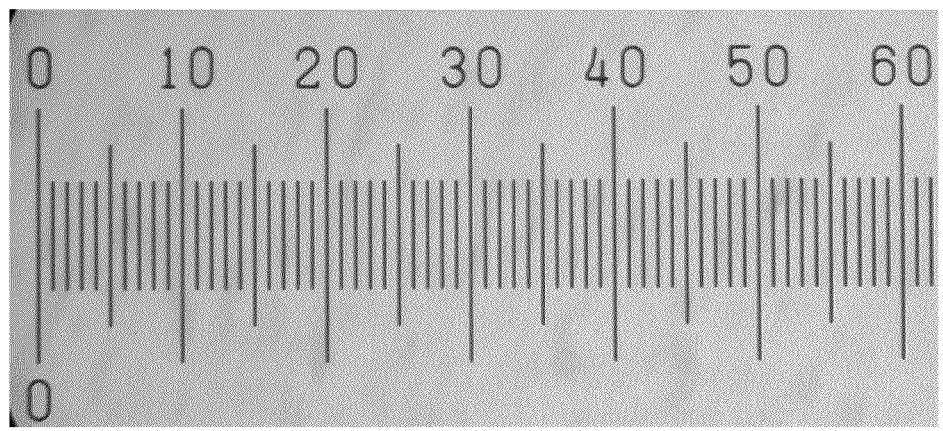
FIG. 9 shows an image of a graticule taken using a 20× objective lens, total magnification 200×, with 10 micron divisions; showing clear resolution to well below 10 microns.

Use of a graticule indicates that oil droplets could be resolved to below 10 microns, and improved resolution is expected by increasing magnification, as shown in FIG. 9. In addition, due to the high intensity of signal conferred by the dye, the droplets are easier to detect; this means that the reliability of the method will be increased, equipment costs reduced, signal to background ratio improved and accuracy of data increased.

8. Monitoring of Water in Oil Using an Aqueous Soluble Dye

Enhancement may be related to dye solubility in water, where insoluble dyes do not fluorescence and soluble dyes do generate fluorescence. Specific examples of dyes whose fluorescence is enhanced in the aqueous phase versus organic phase include polar dyes such as fluorescein, Oregon Green, Cascade Blue, lucifer yellow, Auramine O, tetramethylrhodamine, pysranine, BODIPY FL, Sulforhodamines, Hydroxycoumarins, Polysulfonated Pyrenes, Cyanines, DyLights (Thermo Fisher Scientific), HiLytes (AnaSpec) and AlexaFluor hydrazindes, hydroxylamines and maleimides (Invitrogen). Solvatochromatic dyes may also be used. Dyes which emit in the far red (and so outwith the fluorescence of most oil) are also available and will help reduce background interference from oil. These include Alexa Fluor 633 hydrazide, Alexa Fluor 647 hydrazide and Alexa Fluor 647 hydroxylamine (Invitrogen). Such dyes are highly water soluble, bright and photostable and will be useful for water in oil assessment. Where the pH of the water in the oil has been altered, a pH sensitive dye may be added for detection. For example the pH may be lowered by addition of hydrochloric acid and then a dye such as neutral red or acridine orange, or Polysulfonated Pyrenes such as HPTS added. A signal change will result when the dye is in contact with the water and may be observed as a change in intensity, wavelength or lifetime. For example, Lysosensor probes (Invitrogen) exhibit a pH-dependent increase in fluorescence intensity upon acidification (by protonation of weakly basic side chain leading to fluorescence quenching) and may be used to provide a signal that is enhanced on contact with acid aqueous phase.

Addition of an aqueous soluble dye to a water and oil multiphase mixture allows water in oil to be monitored. 10 µL of 100 µM fluorescein (Sigma) in deionised water was added to 500 µL petroleum ether and the resulting mixture imaged at 125× magnification using a Nikon Fluorescent microscope with FITC filter set (485/535 ex/em). Droplets of water in petroleum ether were visible as bright spherical objects (FIG. 10).

9. Monitoring of Water in Dodecane Samples

A 1 mg/mL (~3 mM) solution of fluorescein (Sigma) in ethanol (Fisher, spectroscopic grade) was diluted ten-fold in deionised water. 50 µL of this solution was added to 1 mL of dodecane (Fluka) and mixed thoroughly by shaking and vortexing. 25 µL of this dispersion was quickly removed and placed on to a standard glass microscope slide and a cover slip was applied.

The microscope was a Nikon Optiphot with epifluorescence optics, a high pressure mercury light source and a FITC filter set (485/535 ex/em). All images were taken with 200× magnification and with a Nikon Coolpix 4500 digital camera. Images have not been adjusted in any way.

Figure 10A:
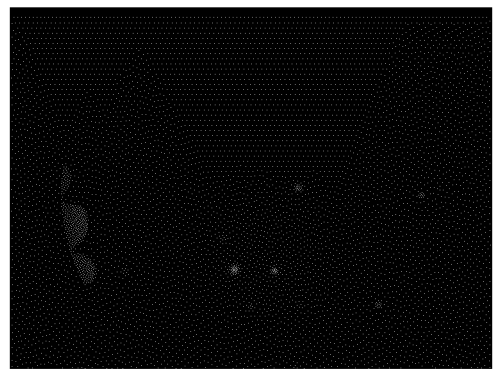
FIGS. 10A and 10B are fluorescence images of two different areas of a single microscope slide containing a mixture of fluorescein dye and dodecane.
Figure 10B:
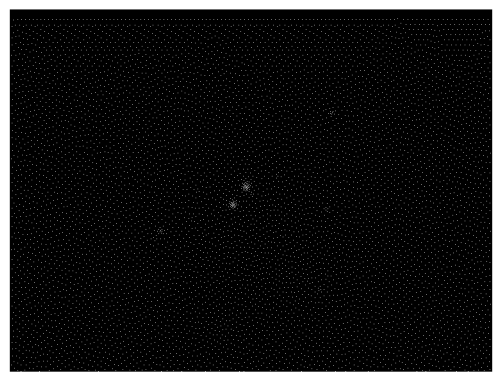
Figure 10C:
FIG. 10C is a bright-field microscopy image of a mixture of fluorescein dye and dodecane.
Figure 10D:
FIG. 10D is a fluorescence microscopy image of the same area of the mixture indicated in FIG. 10C.

Fluorescence images of two different areas of the slide were taken. The dispersed water is observed as green fluorescent particles and the dodecane is non-fluorescent dark areas (FIGS. 10A and 10B)

A bright-field image (FIG. 10C) and a fluorescence image (FIG. 10D) of the same area of slide were taken. Some of the dispersed droplets can be seen under conventional light microscopy but the same images are much more distinct under fluorescence lighting and additional smaller droplets can be observed.

A fluorescence image of pure dodecane without water, showed no significant fluorescence. This confirmed that the fluorescein is capable of marking the water selectively, because it will not emit a signal in the presence of a pure organic sample.

Figure 11:
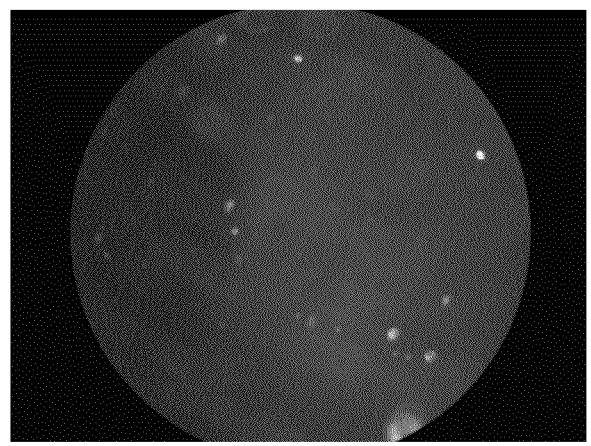
FIG. 11 is a phase-contrast microscopy image of water droplets in dodecane at 200× magnification.

In order to examine droplets of deionised water in dodecane, images were taken at 200× magnification with both phase-contrast illumination (FIG. 11) and fluorescence. The phase-contrast illumination image showed some droplets, but the fluorescence image showed no significant fluorescence. This shows that the signal is not as well enhanced as when a detectable molecule is used as a marker for the aqueous phase.

Figure 12:
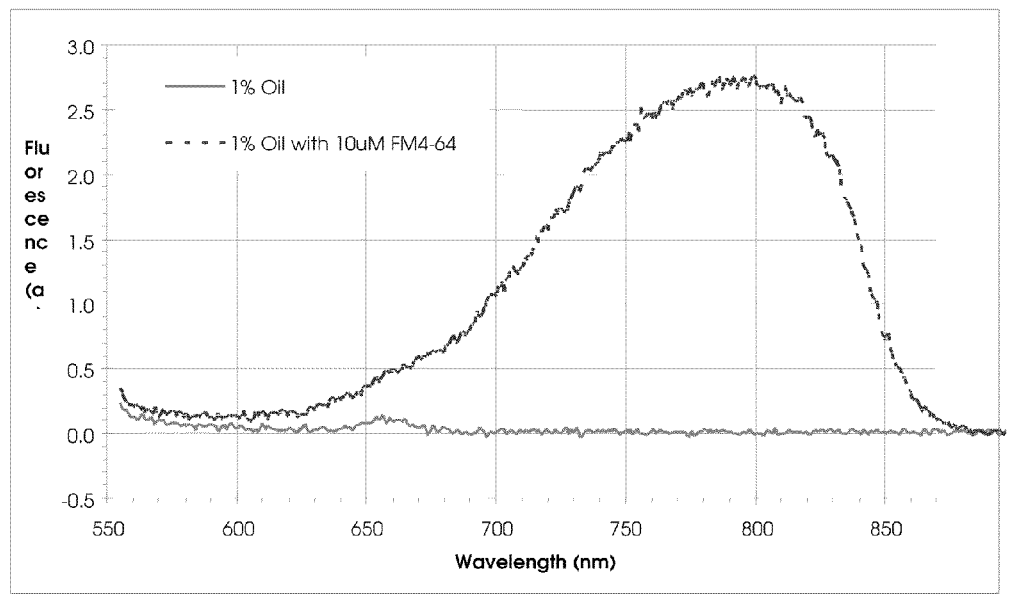
FIG. 12 is a fluorescence emission spectrum of 1% mineral oil standard in deionised water with and without 10 μM of FM 4-64 dye.

10. Use of Lipophilic Dyes at Higher Wavelengths and Uniformity of Response to Oils The lipophilic dyes N-(3-triethylammoniumpropyl)-4-(6-(4-(diethylamino)phenyl)-hexatrienyl)pyridinium dibromide (FM 4-64, Invitrogen) and SRfluor™ 680 Phenyl (Molecular Targeting Technologies Inc.) are selectively soluble in organic over aqueous phases and so they are suitable fluorescent markers for detecting oil in water. They also fluoresce at the red end of the visible spectra where there is much less potential for interferences from other fluorescent species that might be present in the sample. FIG. 12 shows fluorescence spectra of 1% mineral oil standard (Sigma Aldrich) in deionised water with and without 10 µM FM 4-64 dye. The dye is fluorescent in the presence of oil and the oil itself is non-fluorescent at these wavelengths (FIG. 12). The instrument was a Varian Cary Eclipse scanning fluorescence spectrophotometer with 5 nm excitation and emission slits and the excitation wavelength was 540 nm. The unusually large Stokes shift for this fluorescent dye molecule also helped to distinguish dye-related fluorescence from any background.

Figure 13:
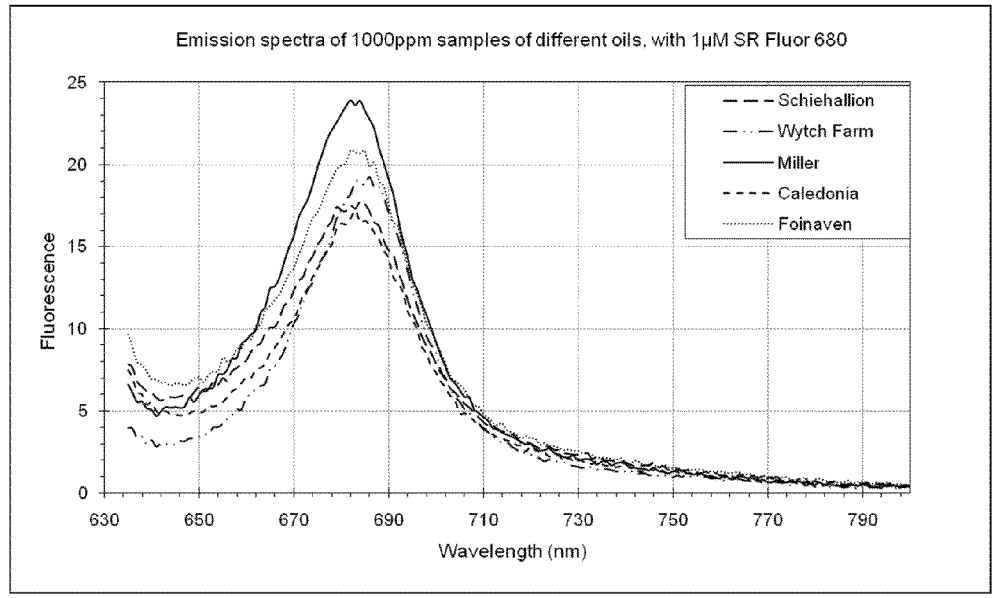
FIG. 13 is a series of fluorescence emission spectra of 1000 ppm of a number of oils in deionised water with 1 μM of SRfluor 680 dye.

SRfluor™ 680 shows extremely good reproducibility across different oil types. Spiked samples of 1000 ppm of various oils in to deionised water showed extremely similar fluorescence emission spectra according to FIG. 13. The instrument settings were as described above but with excitation at 620 nm and SRfluor™ dye at a concentration of 1 µM. The peak min (~640 nm) to peak max (~680 nm) is very similar for all oils. The uniformity of fluorescent response across different oil compositions presents a significant advance in the measurement of oil in water, with potential for drastic reductions in the number of calibrations required and allowing fields with wells from multiple formations to vary composition ratio without significantly affecting results.

Figure 14:
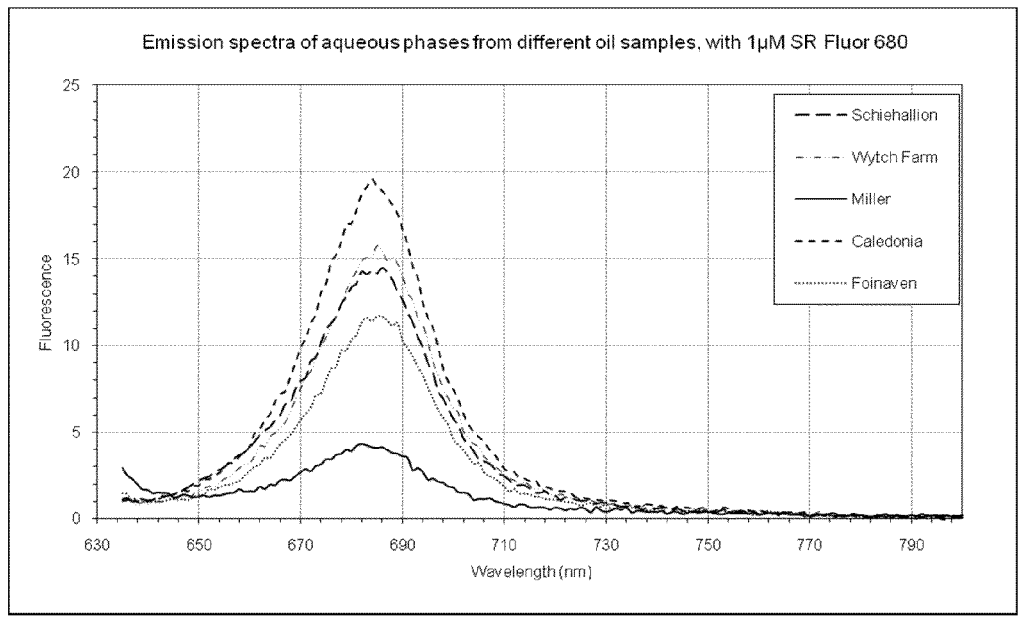
FIG. 14 is a series of fluorescence emission spectra of the aqueous phase from a number of different produced fluid samples with unknown oil concentrations with 1 μM of SRfluor 680 dye.
Figure 15:
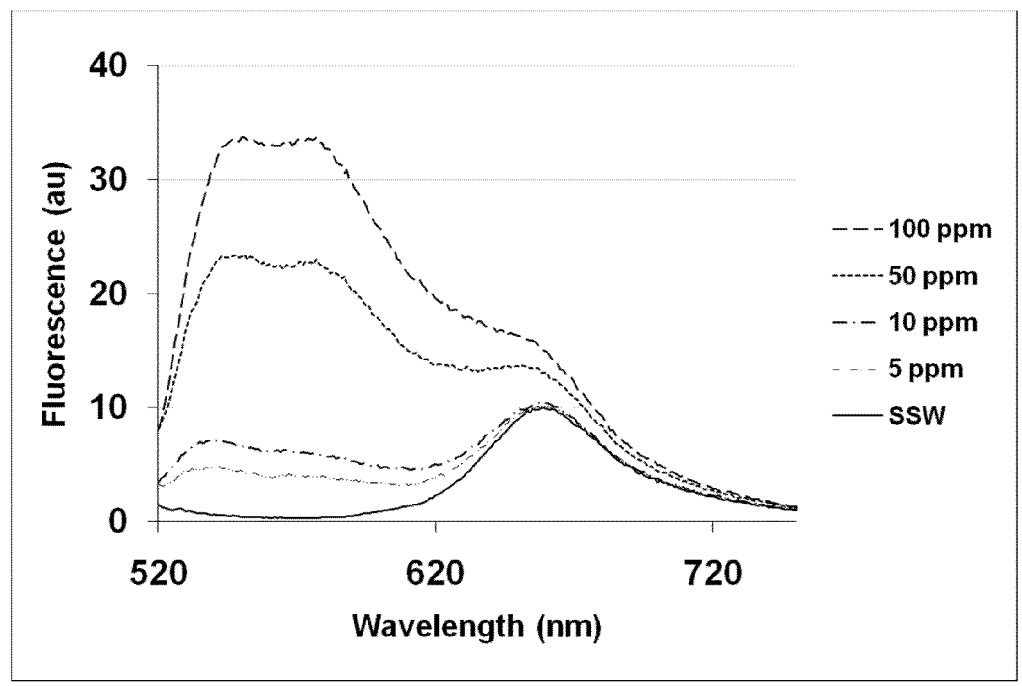
FIG. 15 is a series of fluorescence emission spectra from different spiked concentrations of a North Sea oil in synthetic sea water with 10 μM of Nile Red.
Figure 16:
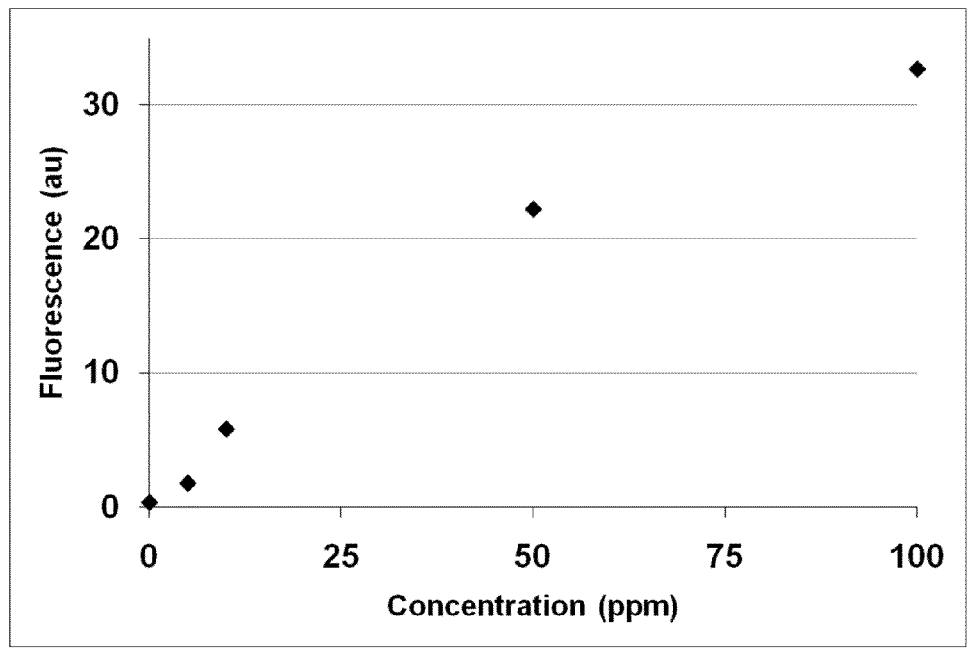
FIG. 16 is a plot of spiked oil concentration versus peak fluorescence intensity for a North Sea oil spiked in to synthetic sea water with 10 μM Nile Red.

The utility of such a dye is demonstrated in FIG. 14 where the aqueous phase of produced fluids from various oilfields was tested in the same way as the spiked samples. The different amounts of entrained oils are related to the different peak fluorescent intensities in the spectra.

11. Concentration-Related Response Curve

Various volumes of a North Sea condensate oil were spiked in to synthetic seawater. The samples were dispersed and then analysed using a fluorescent dye. From a 1 mM ethanolic stock of Nile Red (Sigma Aldrich), samples were analysed at a final dye concentration of 10 µM Nile Red. The stock was added to the test sample and gently mixed before analysing by fluorescence spectroscopy (excitation at 500 nm, slits at 5 nm) on a Varian Carey Eclipse instrument with 1 cm cuvettes. This was repeated for the samples at all different concentrations and the spectra were compared (FIG. 4).

The oil related fluorescence intensity at 580 nm can be plotted as a function of spiked oil concentration (FIG. 5) and a direct relationship can be observed. By creating such a calibration curve for an oil, it can be seen how this method can be used to determine concentration of oil in a water sample. Alternatively, it can be used to correlate against another analysis method, for example where one method is accepted by a regulatory body, by comparing a concentration response curve for each method to create a correlation.

12. Correlation with a Regulatory Method

Instead of using spiked oil in water samples, genuine produced water samples can be used to provide a correlation between the marker method and another method which might be accepted by a regulatory body. Two produced water samples were obtained from a Central North Sea gas-condensate platform. The samples were split with one being analysed by the fluorescent marker method and one being analysed by the GC-FID method according to a modified version of the ISO 9377-2 method which is the reporting method for the OSPAR region.

The fluorescent dye analysis method was as described above with 10 µM Nile Red and the intensity at 580 nm for the tests samples was extracted. Control spectra of the produced water sample with no dye and dye in deionised water were acquired so that the sample intensities could be corrected to just contain the component from the additional intensity resulting from the oil and dye interactions:

Corrected Spectra=Marked PW Spectra−PW Spectra−(Marked Water−Water)

Figure 17:
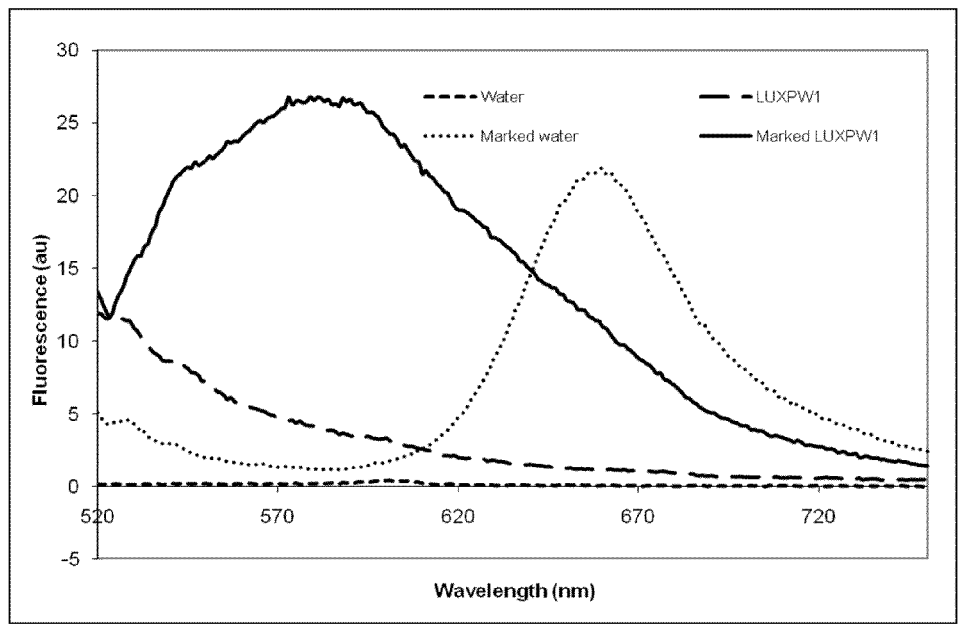
FIG. 17 is a series of fluorescence emission spectra of deionised water and a produced water, each recorded with and without 10 μM Nile Red.
Figure 18:
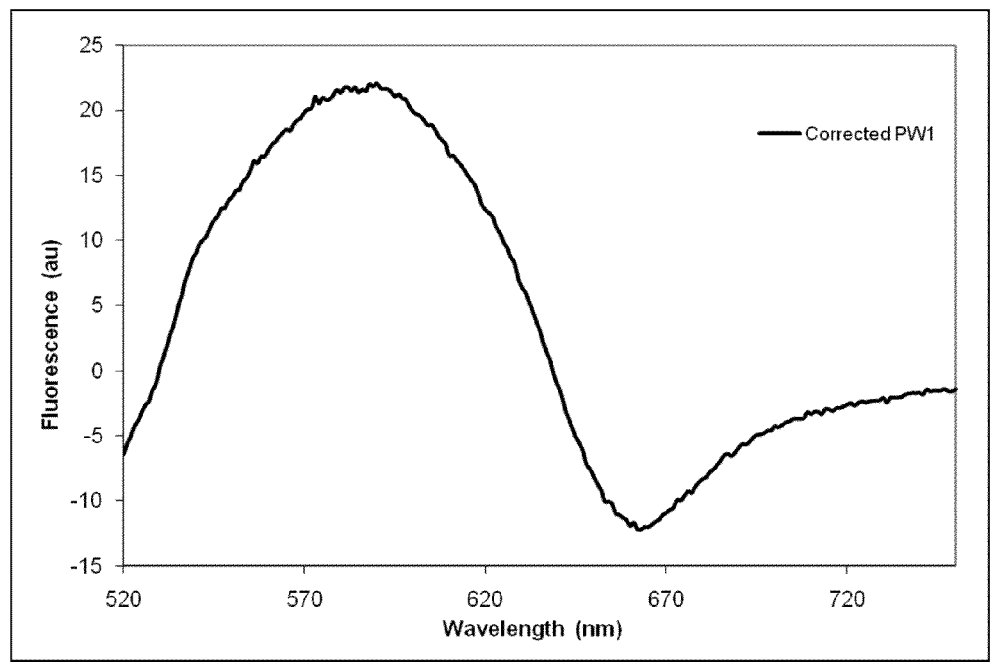
FIG. 18 is a fluorescence emission spectrum of a produced water sample with 10 μM Nile Red, with the components of the intensities due to the control experiments subtracted.

The transformation from the sample and control spectra to a corrected spectrum can be seen in FIGS. 17 and 18. For the two samples, the fluorescence method produced corrected fluorescent intensities of 21.4 and 15.0 arbitrary fluorescence units, and the GC-FID method gave reported results of 21.5 and 13.1 mg/L respectively. By comparing more samples, a correlation curve could be produced, which could then be used to convert fluorescence units in to oil in water values in mg/L correlated to the regulatory method.

13. Optimisation of a Dye for Field Use

Compared to a laboratory environment, sampling and measuring in the field can produce greater challenges, for example, there may be a wide variety of physical and chemical contaminants. In order to be useful in field deployment, a fluorescent marker was analysed in the presence of a number of different chemical environments and under different physical conditions.

Figure 19:
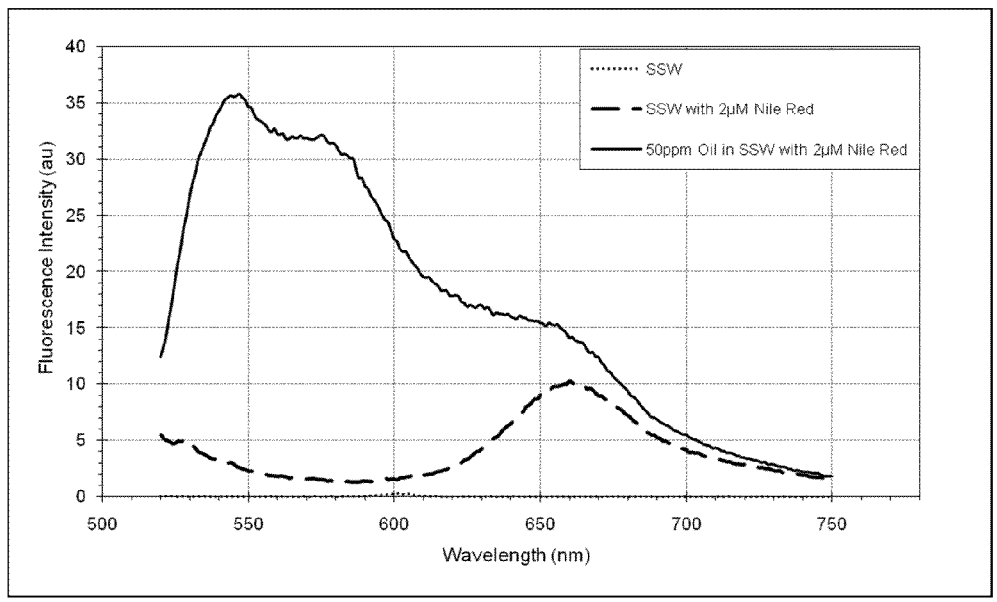
FIG. 19 is a fluorescence emission spectrum of synthetic sea water with and without 2 μM Nile Red and with 50 ppm of oil with 2 μM of Nile Red.

The aqueous portion of produced water can arise from various sources including formation water, sea water and injected water and so it has various degrees of ionic strength. To be most useful, a marker will still function at various different ionic strengths. Synthetic seawater was prepared by dissolving 4.83 g of $Na_2SO_4.10H_2O$, 8.76 g of $CaCl_2.6H_2O$, 7.83 g of $MgCl_2.6H_2O$, 0.79 g of KCl and 49.83 g of NaCl in water to a final volume of 1 L. This was used to prepare a sample of oil in water by spiking with 50 ppm of oil (Britannia field). This sample was mixed with 2 µM of Nile Red and analysed by the same fluorescence method as described above and compared to the synthetic sea water (SSW) and SSW with Nile Red blanks. FIG. 19 shows the comparison of the spectrum and demonstrates that a significant fluorescent response is recorded by the inclusion of oil and demonstrates the capacity of the Nile Red marker to function in different ionic strength media.

Figure 20:
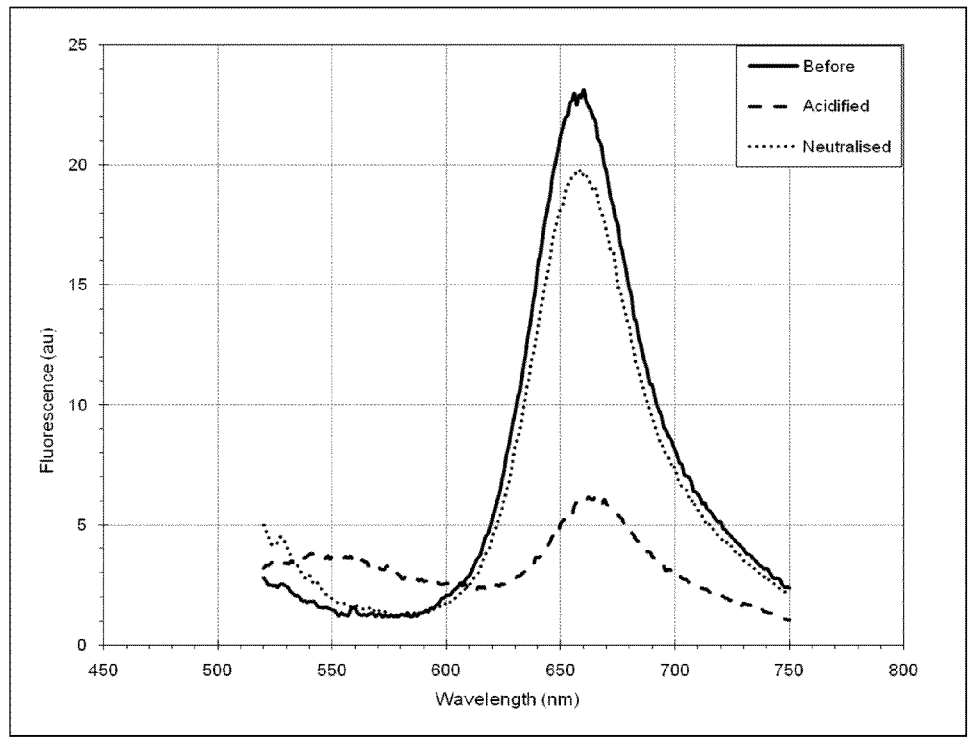
FIG. 20 is a fluorescence emission spectrum of deionised water with 10 ppm Britannia oil and 10 μM Nile Red: as prepared, pH adjusted to pH 1.2 and then adjusted to pH 5.

It is common practice in many offshore facilities to stabilise samples of produced water by acidifying the sample to a very low pH (typically ~pH 1). Acidification is also part of the preparation process for some methods which use a solvent extraction to remove the hydrocarbons from the water—the low pH protonates organic acids and similar materials and makes them more likely to be extracted in the solvent. As these acid samples are often encountered in the field, the effect of low pH on the dye method was investigated. A 10 ppm sample of Britannia oil in deionised water was prepared and the dye method was used to measure the fluorescence response from a sub-sample using 10 µM of Nile Red. The sample was then acidified with hydrochloric acid to a pH of 1.2 and a sub-sample was analysed in the same way. The spectral response was seen to change considerably. Sodium hydroxide was used to bring the sample to pH 5 again and analysis showed that the peak shape returned to the original profile. The spectra are shown in FIG. 20 and demonstrate the possibility of using a buffer to ensure that the sample is within an effective pH range. Analysis of multiple samples suggested that the effective operating pH for Nile Red dye was anything greater than pH 2 (data not shown).

Figure 21:
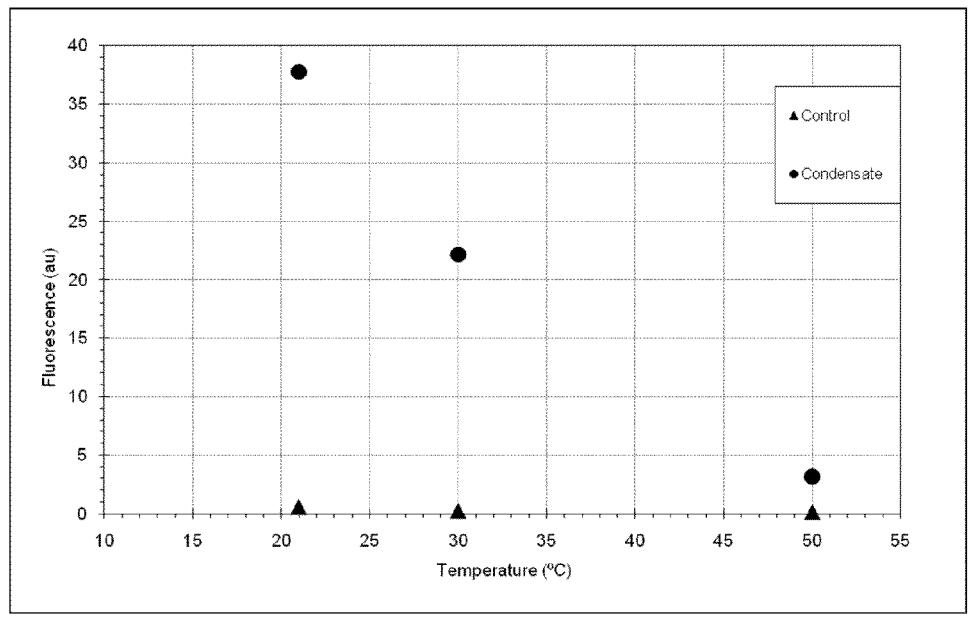
FIG. 21 is a plot of the peak fluorescence intensities of 10 μM Nile Red in deionised water and in 100 ppm condensate in deionised water over a range of temperatures.

Produced water flows in the processing system and experiences a range of temperature according to the stage of process. The range of geographical locations in oil and gas production also means that testing of produced water can occur over a range of temperatures. To investigate the response of the dye technique to this, a 100 ppm sample of condensate in deionised was prepared. It was heated in an oven for one hour and then tested using the dye method with 10 µM Nile Red. The control was just deionised water. The fluorescence intensity for the oil in water sample was seen to decrease with increasing temperature. This may have been as a result in a change in performance of the dye but may have also been related to the increase in solubility of oil with temperature and potential losses from vapour in the head-space at higher temperatures. The results are shown in FIG. 21 and demonstrate that it may be beneficial to regulate the temperature of a sample prior to testing, with room temperature providing good results.

Figure 22:
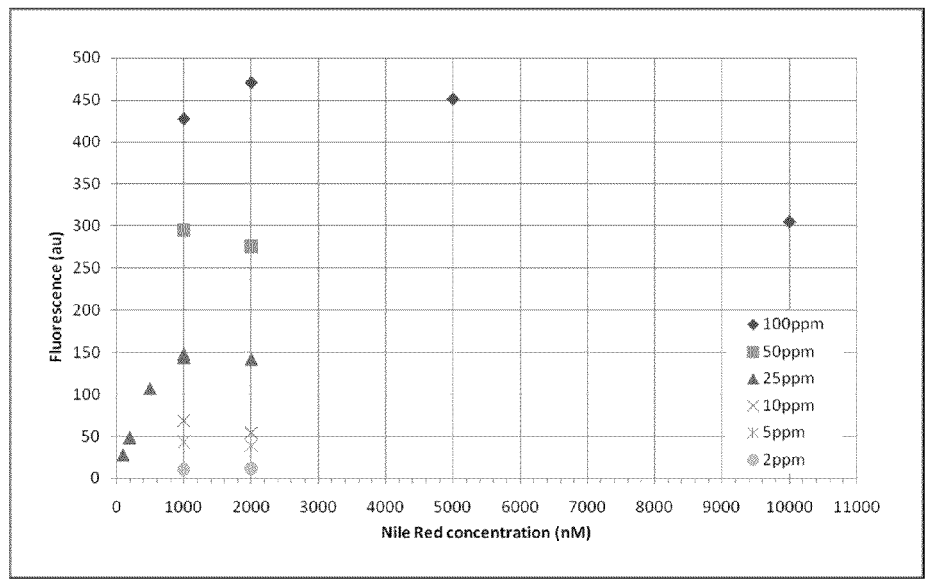
FIG. 22 is a plot of Nile Red concentration versus peak fluorescence intensity for a number of different concentrations of spiked oil in to deionised water.

The nature of the relationship between the dye and the oil droplets means that the fluorescence response of the marker varies with the absolute and relative quantities of each. To determine an unknown concentration of oil, a constant concentration of marker must be used. To investigate the optimum concentration of marker, a concentration range of condensate spiked into deionised water was prepared and tested with a range of different final Nile Red concentrations. FIG. 22 is a graph of the peak intensity versus Nile Red concentration for a variety of condensate concentrations and suggests the 0-100 ppm range typical for produced waters, 1000 nM (1 µM) is optimum.

14. Monitoring Over Time in an Industrial Setting

Figure 23:
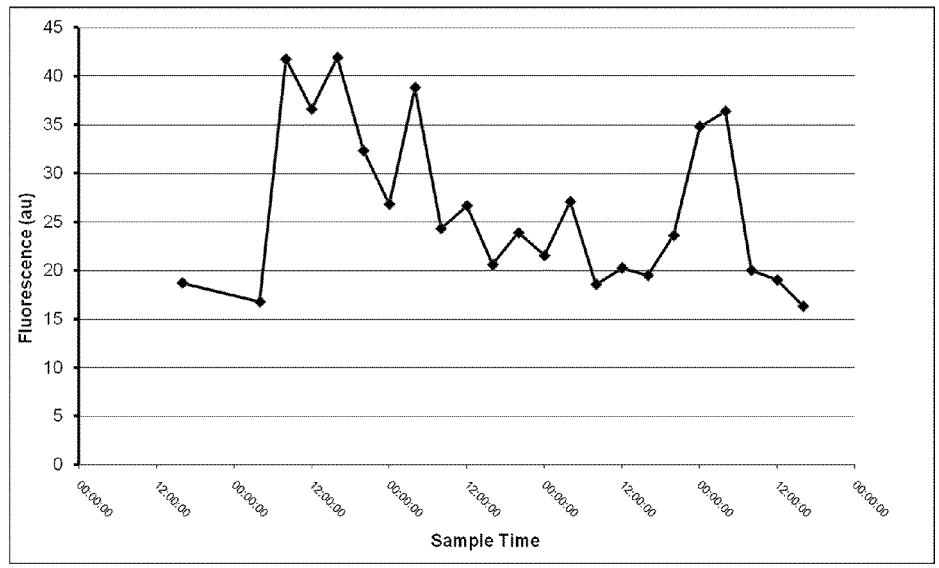
FIG. 23 is a plot of peak fluorescence intensity from samples analysed after addition of 1 μM Nile Red, which had been sampled from the water drain of a crude oil storage tank at various times.

It is normal practice in a continual process, to take regular samples to monitor performance over time. In some cases it is a regulatory requirement to measure samples regularly. The marker method can provide rapid results for such sampling regimes and, to test this, it was used to monitor oil in water trends over time as water was drained from crude oil storage tanks at an oil receiving terminal in the UK. 100 mL samples were drawn from the discharge water line every 4 hours over 4 days. Nile Red at a final concentration of 1 µM was used to report the relative oil levels in each sample using the fluorescence method described above. The results showed the capability of the system for monitoring the trend in oil levels over time with higher fluorescence intensity equating to higher oil levels (FIG. 23).

15. Water in Oil in the Near IR

Crude oils contain components which are fluorescent in the visible range. The degree of fluorescence varies with absolute composition of oil but, generally, darker and heavier oils are more fluorescent than lighter oils and condensates. Experiments were carried out in the far red and near infrared spectrum where the fluorescence is expected to be considerably less pronounced than in the ultra-violet and visible regions.

Two oil samples were spiked with dyed deionised water to simulate a water in oil sample for testing. A marker was chosen which was fluorescent in the mid-red region of the spectrum and was more soluble in water than in oil—Atto 620 (Sigma Aldrich). A solution of 1 mg/mL Atto 620 in deionised water was prepared and added to each oil sample at a concentration of 5% of total volume. The fluorescence was observed on a Nikon DMS fluorescence microscope at 250× magnification and with FITC (Excitation ~490 nm, Emission ~520 nm) and Cy5 (Excitation ~620 nm, Emission ~650 nm) filter sets (Chroma Technology). The samples were placed on a standard fluorescent microscope slide with glass cover-slip for microscopy. One oil sample was a light oil (Brodgar condensate) and the other was a heavier black oil (Brent crude). Images were recorded in colour with a Nikon Coolpix 6500 camera and then converted to greyscale (FIGS. 24 and 25).

Figure 24:
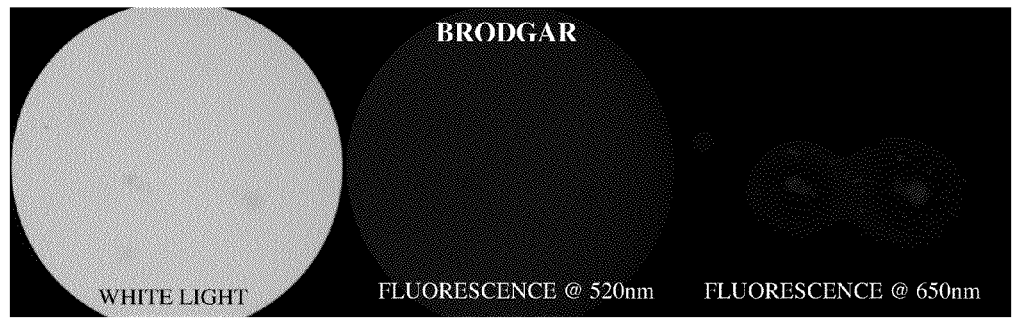
FIG. 24 is a series of images from a fluorescence microscope taken with a digital camera. The sample is Brodgar condensate with 5% deionised water containing 1 mg/mL Atto 620. The images are (from left to right): white light illumination with no optical filters in place, fluorescence illumination from a high pressure mercury lamp with a FITC filter in place and fluorescence illumination with a Cy5 filter in place.

FIG. 24 shows that Brodgar oil is relatively transparent in the thin film formed on a microscope slide because a lot of light passes through the sample when there are no filters in place and a white light source is used to illuminate the sample (image on left of set of three). Some darker patches can be picked out but it is unclear whether or not they are due to water or other particles in solution or in the optical path. The middle image shows the same sample under fluorescence illumination (mercury lamp) with a FITC filter set. In this region of the spectrum (green) the oil is slightly fluorescent and the light emitted from the background oil means that there is little scope to distinguish dye fluorescence from aqueous droplets. The picture on the right is also under fluorescence illumination but with a Cy5 filter set. At this red wavelength the condensate does not fluoresce to any significant degree but the dyed water can be discriminated from the background due to the dye fluorescence.

Figure 25:
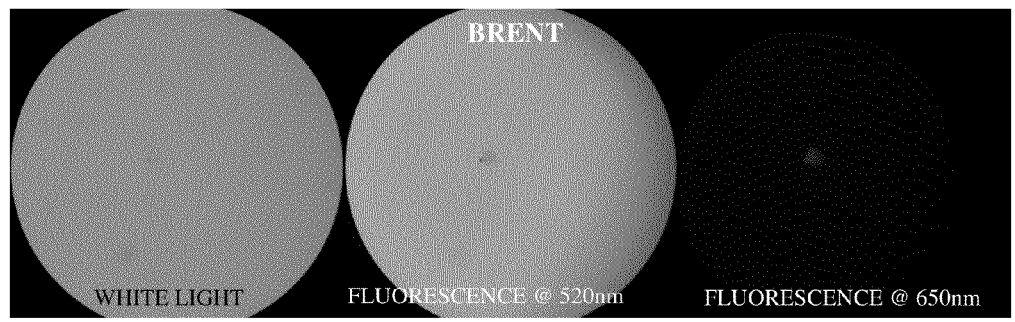
FIG. 25 is a series of images from a fluorescence microscope taken with a digital camera. The sample is Brent crude with 5% deionised water containing 1 mg/mL Atto 620. The images are (from left to right): white light illumination with no optical filters in place, fluorescence illumination from a high pressure mercury lamp with a FITC filter in place and fluorescence illumination with a Cy5 filter in place.

FIG. 25 shows the same set of images for a sample of Brent crude oil. The darker oil is less transparent under white light illumination (less intense light on left image) but it is more fluorescent than the condensate (middle and right image show greater light emitted from oil).

These experiments demonstrate that using fluorescent dyes to measure water in oil is a viable method. The fluorescence of oil at lower wavelengths means that contrast between dyed water and oil becomes greater at higher wavelengths. Red dyes may be suitable for measuring water in condensates but darker oils still fluoresce slightly.

Figure 26:
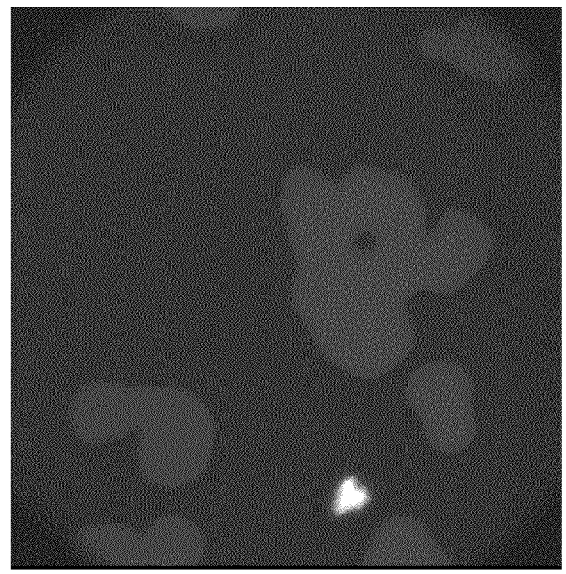
FIG. 26 is a (contrast enhanced) photograph of a sample of Brent crude with 5% deionised water containing 1 mg/mL Atto 740 between a microscope slide and glass cover slip, taken on a fluorescence microscope at 250× magnification and through a Cy7 optical filter set.

A camera with a red-sensitive CCD (UVP) was used to measure fluorescence at a higher wavelength in order to test a water soluble dye that fluoresced in the near-IR. A 1 mg/mL aqueous solution of Atto 740 was added to Brent Crude to 5% by volume. After shaking, a sample of this was placed on a glass microscope slide and a fluorescence image was obtained using the camera on the fluorescence microscope at 250× magnification. The filter set was Cy7 (Excitation ~740 nm, Emission ~800 nm). The image (FIG. 26) demonstrates that the very low background fluorescence from the crude oil at this wavelength and the dyed water is easy to distinguish by fluorescence.

Figure 27:
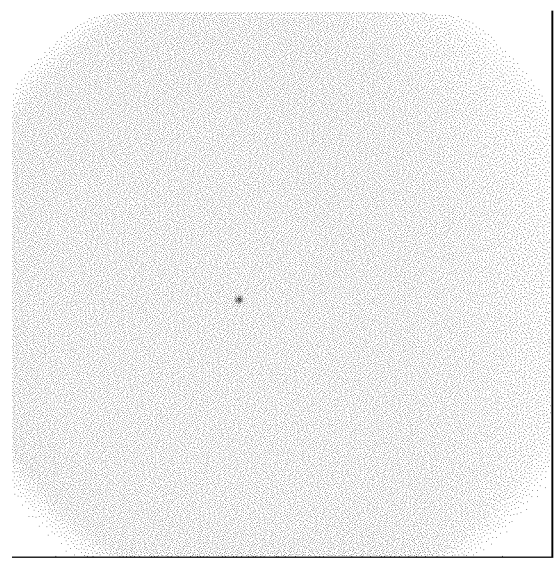
FIG. 27 is a photograph of a sample of Britannia crude with 1% deionised water after mixing with ~50 μg of Atto 740, for which the colours have been inverted. The sample was mounted on a microscope slide with glass cover slip and then analysed on a fluorescence microscope at 250× magnification and through a Cy7 optical filter set.

In order to simulate a testing protocol that would be more useful in industrial settings, a sample of water in oil was prepared by adding deionised water to Britannia oil at a concentration of 1% by volume. After shaking, this mixture was added to a tube containing a small amount of Atto 740 powder (<1 mg, estimated ~50 µg). The fluid was then imaged on a fluorescence microscope through a Cy7 filter set. The image of the results shown in FIG. 27 demonstrates the efficacy of this method for discriminating water from oil.

To test the water soluble dyes for measuring water in oil in spectroscopic mode, a fluorescence spectrophotometer (Varian Cary Eclipse) used to analyse a water in oil emulsion with and without the fluorescent dye (Atto 740). The emulsion was created by mixing Britannia condensate with 500 ppm deionised water. The sample was placed in a 1 cm quartz cuvette and shaken to disperse. The two phases were found to separate very quickly and the water sank to the bottom of the cuvette so the sample could not be measured as the light path of the fluorescence spectrophotometer passed through the oil phase only. A surfactant solution (1% weight by volume of sodium dodecyl sulphate in deionised water) was prepared and a small amount (0.03% by volume) was added to the sample to create an emulsion. After addition of the aqueous surfactant, the total water concentration was 800 ppm. After shaking the two phases were seen to be dispersed well and the solution was optically opaque.

Figure 28:
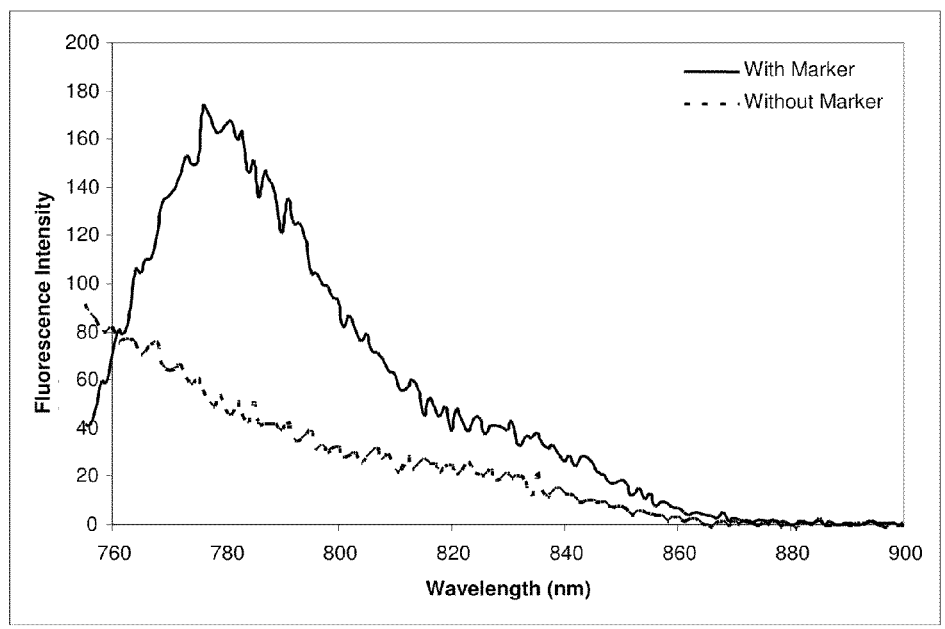
FIG. 28 is a fluorescence emission spectrum of Britannia oil with deionised water in a surfactant-stabilised microemulsion, with and without Atto 740 marker.

A fluorescence emission spectrum was recorded with excitation at 740 nm. A small amount of Atto 740 powder (<1 mg, estimate ~50 µg) was added to the cuvette and it was mixed by inverting several times before acquiring a fluorescence emission spectrum with the same settings. FIG. 28 shows the two spectra—the opacity of the fluid is demonstrated by the large amount of scattered light in both samples, but the sample with the dye does display an increased fluorescence with a peak ~780 nm. This confirms the viability of using a spectroscopic approach to measure water in oil using fluorescence markers.

The invention claimed is:

1. A method for the assessment of a multiphase sample taken from an oil, gas or water production, processing or treatment facility, the multiphase sample comprising an aqueous phase and an organic phase, the method comprising:

a. adding at least one detection molecule to the multiphase sample to create a mixture containing the at least one detection molecule and the multiphase sample;
   b. detecting a signal emitted from the mixture, the signal being detectably different when the at least one detection molecule is present in one of either the organic phase, the aqueous phase or an interface between the organic phase and the aqueous phase of the multiphase sample; and
   c. analysing the detected signal to assess the properties of the organic phase, the aqueous phase or the interface between said organic phase and said aqueous phase; and
   d. analyzing the detected signal to assess a particle size distribution and/or a droplet size distribution of either said organic phase or said aqueous phase.

2. A method according to claim 1, further comprising the step of irradiating the multiphase sample with electromagnetic radiation prior to detection of the signal.

3. A method according to claim 1, further comprising the step of subjecting the multiphase sample to ultrasonic sound waves, adding a surfactant to the multiphase sample and/or subjecting the multiphase sample to shear forces prior to addition of the at least one detection molecule, after addition of the detection molecule but prior to detecting a signal emitted from the mixture or both prior to addition of the at least one detection molecule and after addition of the detection molecule but prior to detecting a signal emitted from the mixture.

4. A method according claim 1, wherein the at least one detection molecule is dispersed throughout the organic phase and the aqueous phase of the multiphase sample and will emit a signal only on an interaction with one of the organic phase, the aqueous phase or the interface between the organic phase and the aqueous phase.

5. A method according to claim 4, wherein the at least one detection molecule emits a detectable fluorescence change due to a difference in an induced dipole moment between a ground state and an excited state that results from the type of molecules in an environment surrounding the at least one detection molecule.

6. A method according to claim 1, wherein the at least one detection molecule is hydrophilic.

7. A method according to claim 1, wherein the at least one detection molecule is hydrophobic.

8. A method according to claim 1, further comprising the step of processing the mixture so that the at least one detection molecule is dispersed throughout at least one phase of the multiphase sample before the signal detection step.

9. A method according to claim 1, wherein the at least one detection molecule interacts with either the organic phase or the aqueous phase or the interface between said organic and aqueous phases via hydrogen bonding, electrostatic interactions, Van der Waals forces, London forces, ionic forces, hydrophobic interactions or a combination thereof.

10. A method according to claim 1, wherein the signal is emitted at a wavelength of electromagnetic radiation that is different to a background signal.

11. A method according to claim 1, wherein the signal is measurable by a detectable change in the intensity of electromagnetic radiation.

12. A method according to claim 10, wherein the electromagnetic radiation is in the infrared spectrum.

13. A method according to claim 1, wherein the signal has an electromagnetic radiation lifetime that is detectably different to a background signal.

14. A method according to claim 13, wherein the fluorescence lifetime characteristics of the signal are detectably different to the fluorescence lifetime characteristics of the background signal.

15. A method according to claim 1, wherein the fluorescence polarisation characteristics of the signal are detectably different to the fluorescence polarisation characteristics of a background signal.

16. A method according to claim 1, wherein the signal comprises a change in colour.

17. A method according to claim 1, wherein a property of at least one of the phases is altered to enhance detection of the at least one of the phases.

18. A method according to claim 17, wherein the pH of at least one of the phases is altered by addition of acid or base.

19. A method according to claim 17, wherein the relative solubility of the at least one detection molecule is altered using host-guest chemistry.

20. A method according to claim 1, wherein the at least one detection molecule is at least one dye.

21. A method according to claim 20, wherein the dye is a solvatochromatic dye.

22. A method according to claim 20, wherein an optical signal emitted by the dye is detected and analysed.

23. A method according to claim 22, wherein the analysed optical signal is used to determine the concentration of treatment chemicals.

24. A method according to claim 20, wherein the dye is selected from phenoxazone dyes, dialkylcarbocyanines and pyridium betaine dyes.

25. A method according to claim 20, wherein the dye is Nile Red.

26. A method according to claim 1, wherein the at least one detection molecule comprises a Fluorescence Resonance Energy Transfer (FRET) pair.

27. A method according to claim 1, wherein the property of the phase that is assessed in step c is its volume in the multiphase sample.

28. A method according to claim 1, wherein the concentration of the at least one detection molecule and consequent proximity to and interaction with other detection molecules causes a signal change in intensity or wavelength.

29. A method according to claim 28, wherein the at least one detection molecule and at least one of the other detection molecules are two members of one FRET pair.

30. A method according to claim 2, wherein the electromagnetic radiation is provided by a laser, an LED, or a flash lamp.

31. A method according to claim 1, wherein the signal is detected using a fluorescence detector, optical microscope, charge coupled device (CCD) camera, complementary metal oxide semiconductor (CMOS) camera, charged injection device (CID), photographic film, fibre-optic device, photometric detector, micro electro mechanical sensor (MEMS) device, single photon detector, spectrophotometer, spectrofluorometer, luminometer, system or by eye.

32. A method according to claim 1, wherein the phase or the interface between phases is assessed in-line.

33. A method according to claim 1, wherein the phase or the interface between phases is assessed off-line.

34. A method according to claim 1, wherein the phase or the interface between phases is assessed at-line.

35. A method according to claim 1, wherein the phase or the interface between phases is assessed on-line.

36. A method according to claim 1, wherein the at least one detection molecule is non-toxic.

37. A method according to claim 1, wherein the at least one detection molecule is stable for at least one month.

38. A method according to claim 1, wherein the at least one detection molecule is selected from the group consisting of: phenoxazone dyes; carbocyanines; pyridinium betaine dyes; lipophilic carbocyanines: 1,1'-dioctadecyl-3,3,3',3'-tetramethyl-indocarbocyanine perchlorate (DiI), 3,3'-dioctadecyloxacarbo-cyanine perchlorate (DiO), 1,1'-dioctadecyl-3,3,3',3'-tetramethylindodicarbocyanine perchlorate (DiD), 1,1'-dioctadecyl-3,3,3',3'-tetramethyl-indotricarbocyanine iodide (DiR) and their derivatives; 1,6-diphenyl-1,3,5-hexatriene (DPH); trimethylammonium-DPH (TMA-DPH); 2-anilinonaphthalene-6-sulfonic acid (2,6-ANS) or bis-ANS; laurdan; 3,3'-dipentyloxacarbocyanine iodide ($DiOC_5$) and 3,3'-dihexyloxacarbocyanine iodide ($DiOC_6$); Invitrogen FM dyes 1-43, 4-64; Invitrogen dye RH 414 and NanoOrange reagent; disodium salt of 4-amino-4'-benzamidostilbene-2,2'-disulfonic acid (MBDS or BADS), diethylthiatricarbocyanine iodide (DTTCI); 4,5-benzoindotricarbocyanine (IR-125); N,N-dimethylaminobenzonitrile (DMABN); nitrobenzoxadiazole (NBD) labelled phosphocholine; octadecyl rhodamine B; benzophenoxazine-2-one; merocyanine 540; 4-(4-(pentadecylamino) styryl-N-methylpyridinium iodide (di-15-ASP); 3,3'-dihexadecylthiadicarbocyanine iodide (diSC16(5)); octadecyl acridine orange; difluoroboradiaza-s-indacenes and derivatives; heterocyclic moieties or electron donating groups; solvatochromatic dyes; symmetrical tricarbocyanine near IR dyes; rylenes; squaraines; squaraine-rotaxanes; difluoro-boradiaza-s-indacenes and quantum dots.

39. A method according to claim 1, wherein the at least one detection molecule is selected from the group consisting of: fluorescein; Oregon Green; Cascade Blue; lucifer yellow; Auramine O; tetramethylrhodamine; pysranine; boron dipyrromethene difluoride (BODIPY FL); Sulforhodamines; Hydroxycoumarins; Polysulfonated Pyrenes; Cyanines; DyLights (Thermo Fisher Scientific); HiLytes (AnaSpec); AlexaFluor hydrazindes; Alexa Fluor 633 hydrazide; Alexa Fluor 647 hydrazide; and Alexa Fluor 647 hydroxylamine (Invitrogen); hydroxylamines; maleimides (Invitrogen); solvatochromatic dyes; neutral red or acridine orange; Polysulfonated Pyrenes; Lysosensor probes (Invitrogen); Quantum dots.

40. A method according to claim 4, wherein the at least one detection molecule is selected from the group consisting of phenoxazone dyes, carbocyanines and pyridinium betaine dyes.

41. A method according to claim 1, wherein the property of the phase that is assessed in step c is its concentration in the multiphase sample.

42. A method for the assessment of a multiphase sample taken from an oil, gas or water production, processing or treatment facility, the multiphase sample comprising an emulsion, the method comprising:
   a. adding at least one detection molecule to the multiphase sample to create a mixture containing the at least one detection molecule and the multiphase sample;
   b. detecting a signal emitted from the mixture;
   c. analysing the detected signal to assess the properties of the emulsion; and
   d. analysing the detected signal to assess particle size distribution and/or droplet size distribution of the emulsion.

43. The method of claim 42, wherein the emulsion is oil in water.

44. The method of claim 42, wherein the emulsion is water in oil.

45. The method of claim 42, wherein the emulsion is assessed in-line.

46. The method of claim 42, wherein the emulsion is assessed off-line.

47. A method for screening corrosion inhibitors for their emulsion forming properties, the method comprising:
  a. creating a multiphase sample taken from an oil, gas or water production, processing or treatment facility and containing the corrosion inhibitor of interest,
  b. adding at least one detection molecule to the multiphase sample to create a mixture containing the at least one detection molecule and the multiphase sample;
  c. detecting a signal emitted from the mixture;
  d. analysing the detected signal to assess the properties of the corrosion inhibitor; and
  e. analysing the detected signal to assess particle size distribution and/or droplet size distribution of the emulsion.

* * * * *